(12) United States Patent
Aravalli

(10) Patent No.: US 11,678,885 B2
(45) Date of Patent: Jun. 20, 2023

(54) CIRCULAR STAPLING DEVICE AND METHOD OF USE

(71) Applicant: Covidien LP, Mansfield, MA (US)

(72) Inventor: AVVLN Srinivasa Murthy Aravalli, Hyderabad (IN)

( * ) Notice: Subject to any disclaimer, the term of this patent is extended or adjusted under 35 U.S.C. 154(b) by 900 days.

(21) Appl. No.: 16/479,643

(22) PCT Filed: Mar. 21, 2017

(86) PCT No.: PCT/US2017/023353
§ 371 (c)(1),
(2) Date: Jul. 22, 2019

(87) PCT Pub. No.: WO2018/140066
PCT Pub. Date: Aug. 2, 2018

(65) Prior Publication Data
US 2021/0353294 A1 Nov. 18, 2021

(30) Foreign Application Priority Data
Jan. 25, 2017 (IN) .............................. 201741002959

(51) Int. Cl.
*A61B 17/072* (2006.01)
*A61B 17/11* (2006.01)
(Continued)

(52) U.S. Cl.
CPC .... *A61B 17/1114* (2013.01); *A61B 17/07292* (2013.01); *A61B 17/1155* (2013.01);
(Continued)

(58) Field of Classification Search
CPC .......... A61B 17/1114; A61B 17/07292; A61B 17/1155; A61B 2017/00424;
(Continued)

(56) References Cited

U.S. PATENT DOCUMENTS

| 3,193,165 A | 7/1965 | Akhalaya et al. |
| 3,388,847 A | 6/1968 | Kasulin et al. |

(Continued)

FOREIGN PATENT DOCUMENTS

| CA | 908529 A | 8/1972 |
| CA | 2805365 A1 | 8/2013 |

(Continued)

OTHER PUBLICATIONS

European Search Report dated Apr. 17, 2020, issued in EP Appln. No. 19207263, 9 pages.

(Continued)

*Primary Examiner* — Robert F Long
(74) *Attorney, Agent, or Firm* — Carter, DeLuca & Farrell LLP

(57) ABSTRACT

A circular stapling device is described that is particularly suited for creating stomas. The circular stapling device includes two tool assemblies. The first tool assembly is adapted to create a reinforced incision in tissue, e.g., the rectus sheath, through which a vessel portion, e.g., colon, small intestine, etc. can be pulled through during a surgical procedure. The second tool assembly is adapted to attach a stomal sleeve within the vessel portion such that the stomal sleeve extends from the stoma.

9 Claims, 17 Drawing Sheets

(51) Int. Cl.
*A61B 17/115* (2006.01)
*A61F 5/445* (2006.01)
*A61B 17/00* (2006.01)

(52) U.S. Cl.
CPC .... *A61F 5/445* (2013.01); *A61B 2017/00424* (2013.01); *A61B 2017/07257* (2013.01); *A61B 2017/07285* (2013.01); *A61B 2017/1135* (2013.01)

(58) Field of Classification Search
CPC ........... A61B 2017/07257; A61B 2017/07285; A61B 2017/1135; A61B 2017/0042; A61B 2017/00473; A61B 2017/1139; A61B 2090/0811; A61F 5/445
USPC .............................................. 227/175.1–182.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A * | 6/1980 | Becht .................. A61B 17/115 227/76 |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A * | 4/1983 | Gravener ............. A61B 17/115 227/156 |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A * | 6/1987 | Barker .................. A61B 17/115 227/19 |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A * | 1/1990 | Green .................. A61B 17/115 227/180.1 |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,269,794 A * | 12/1993 | Rexroth ........... A61B 17/32002 606/167 |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,383,880 A * | 1/1995 | Hooven .................. A61B 34/76 606/213 |
| 5,392,979 A | 2/1995 | Green et al. |
| 5,395,030 A | 3/1995 | Kuramoto et al. |
| 5,395,033 A * | 3/1995 | Byrne .............. A61B 17/07207 227/19 |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,824 A * | 10/1995 | Fontayne ............. A61B 17/115 606/154 |
| 5,454,825 A | 10/1995 | Van Leeuwen et al. |
| 5,464,415 A | 11/1995 | Chen |
| 5,470,006 A | 11/1995 | Rodak |
| 5,474,223 A * | 12/1995 | Viola .................. A61B 17/115 227/19 |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,742 A * | 2/1998 | Zacharias ............. A61B 17/29 606/1 |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |

(56) References Cited

U.S. PATENT DOCUMENTS

| | | |
|---|---|---|
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 * | 1/2005 | Whitman ......... A61B 17/07207 227/176.1 |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |

(56) References Cited

U.S. PATENT DOCUMENTS

| | | | |
|---|---|---|---|
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,710 B1 * | 9/2010 | Hung ............... B25C 3/004 173/90 |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,540,132 B2 | 9/2013 | Marczyk et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,684,253 B2 * | 4/2014 | Giordano ............ A61B 17/295 227/19 |
| 8,733,611 B2 | 5/2014 | Milliman |
| 9,010,608 B2 * | 4/2015 | Casasanta, Jr. .. A61B 17/07292 227/176.1 |
| 10,478,189 B2 * | 11/2019 | Bear ................. A61B 17/1155 |
| 10,709,452 B2 * | 7/2020 | DiNardo ........... A61B 17/1155 |
| 2001/0000903 A1 * | 5/2001 | Heck ................. A61B 17/1114 227/176.1 |

(56) References Cited

U.S. PATENT DOCUMENTS

| | | | |
|---|---|---|---|
| 2002/0025243 A1* | 2/2002 | Heck | A61B 17/0644 411/457 |
| 2003/0111507 A1 | 6/2003 | Nunez | |
| 2004/0073090 A1 | 4/2004 | Butler et al. | |
| 2005/0051597 A1 | 3/2005 | Toledano | |
| 2005/0107813 A1 | 5/2005 | Gilete Garcia | |
| 2005/0131390 A1* | 6/2005 | Heinrich | A61B 17/07207 606/1 |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2006/0273135 A1* | 12/2006 | Beetel | A61B 17/128 227/175.1 |
| 2006/0278680 A1* | 12/2006 | Viola | A61B 17/068 227/176.1 |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2007/0118157 A1* | 5/2007 | Zuidema | A61B 46/30 606/153 |
| 2008/0185419 A1* | 8/2008 | Smith | A61B 17/07207 227/179.1 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0069942 A1* | 3/2010 | Shelton, IV | A61B 17/07207 227/175.1 |
| 2010/0084453 A1 | 4/2010 | Hu | |
| 2010/0096431 A1* | 4/2010 | Smith | A61B 17/00 227/175.2 |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2011/0278346 A1 | 11/2011 | Hull et al. | |
| 2011/0290851 A1* | 12/2011 | Shelton, IV | A61B 17/07207 227/176.1 |
| 2012/0055972 A1* | 3/2012 | Marczyk | A61B 17/07207 227/175.1 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2015/0053743 A1* | 2/2015 | Yates | A61B 17/068 227/176.1 |
| 2015/0083774 A1* | 3/2015 | Measamer | A61B 17/068 227/175.1 |
| 2015/0351769 A1* | 12/2015 | Lee | A61B 17/1155 227/179.1 |
| 2016/0143641 A1 | 5/2016 | Sapienza et al. | |
| 2016/0157856 A1 | 6/2016 | Williams et al. | |
| 2016/0174988 A1 | 6/2016 | D'Agostino et al. | |
| 2016/0192934 A1 | 7/2016 | Williams et al. | |
| 2016/0192938 A1 | 7/2016 | Sgroi, Jr. | |
| 2016/0302792 A1 | 10/2016 | Motai | |
| 2018/0008272 A1 | 1/2018 | Sgroi, Jr. | |
| 2018/0085124 A1* | 3/2018 | Nativ | A61B 17/07292 |
| 2018/0168635 A1* | 6/2018 | Shelton, IV | A61B 17/29 |
| 2019/0125455 A1* | 5/2019 | Shelton, IV | A61B 17/1155 |
| 2019/0133588 A1* | 5/2019 | Aravalli | A61F 5/445 |
| 2021/0169487 A1* | 6/2021 | Nicholas | A61B 17/1155 |
| 2022/0225995 A1* | 7/2022 | Nicholas | A61B 90/08 |

FOREIGN PATENT DOCUMENTS

| | | |
|---|---|---|
| CN | 103536329 A | 1/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1588667 A1 | 10/2005 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2620105 A1 | 7/2013 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |

(56) References Cited

FOREIGN PATENT DOCUMENTS

| WO | 98/35614 A1 | 8/1998 |
| WO | 0154594 A1 | 8/2001 |
| WO | 2008107918 A1 | 9/2008 |

OTHER PUBLICATIONS

Partial European Search Report dated Oct. 15, 2020, issued in corresponding EP Appln. No. 17894018, 13 pages.
Chinese Office Action dated Dec. 27, 2021, issued in corresponding Chinese Appln. No. 201780083140, 11 pages.

* cited by examiner

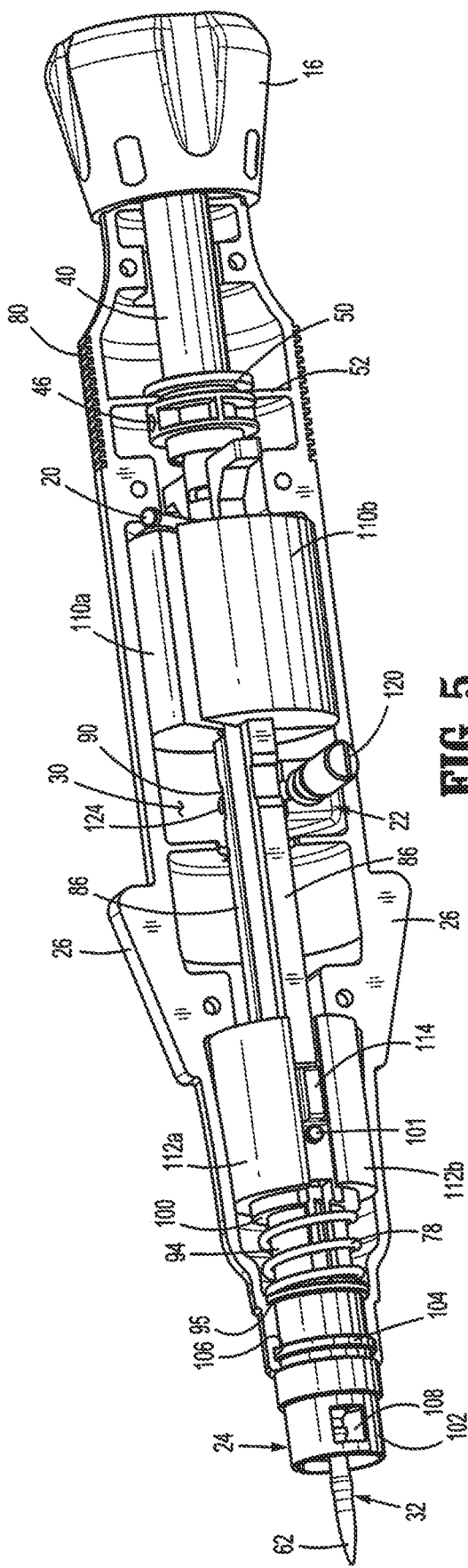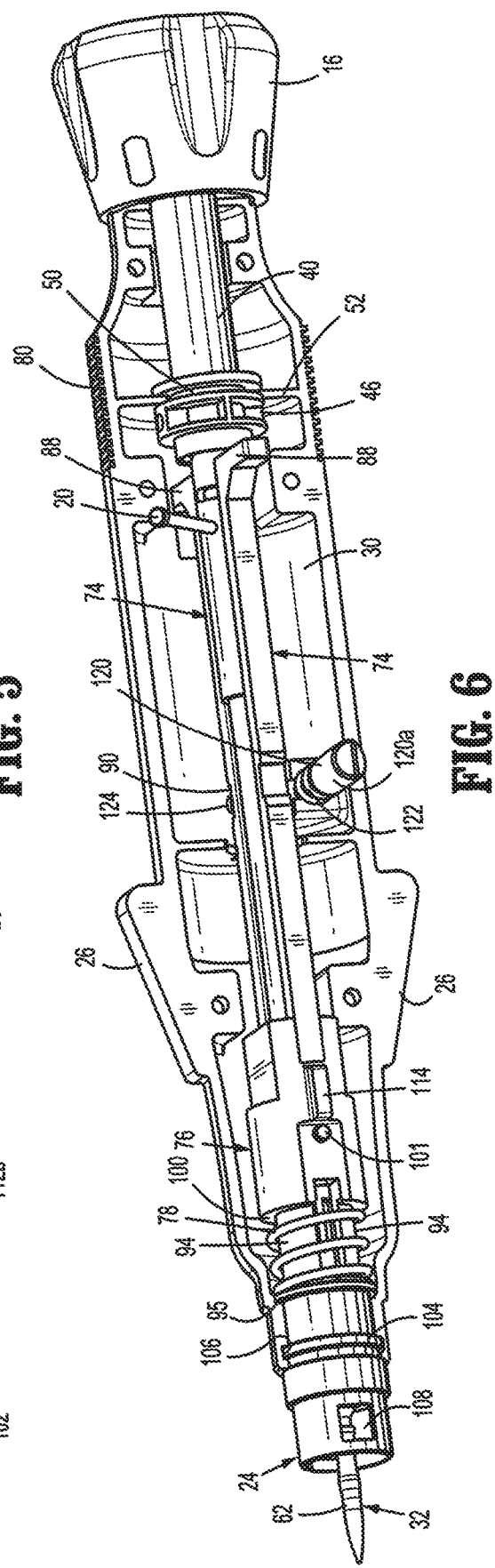

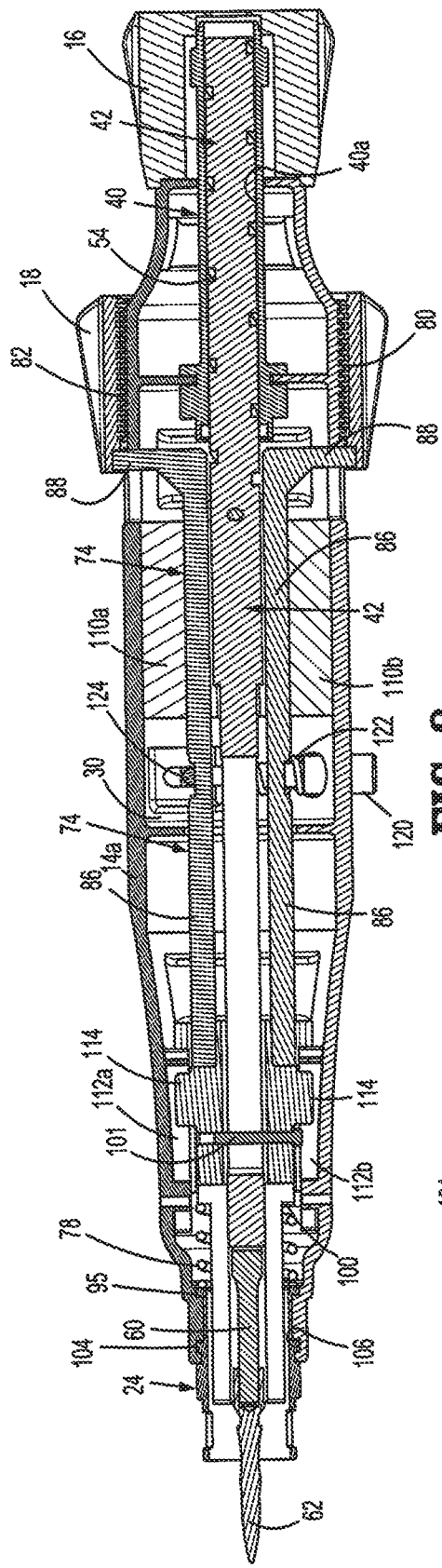

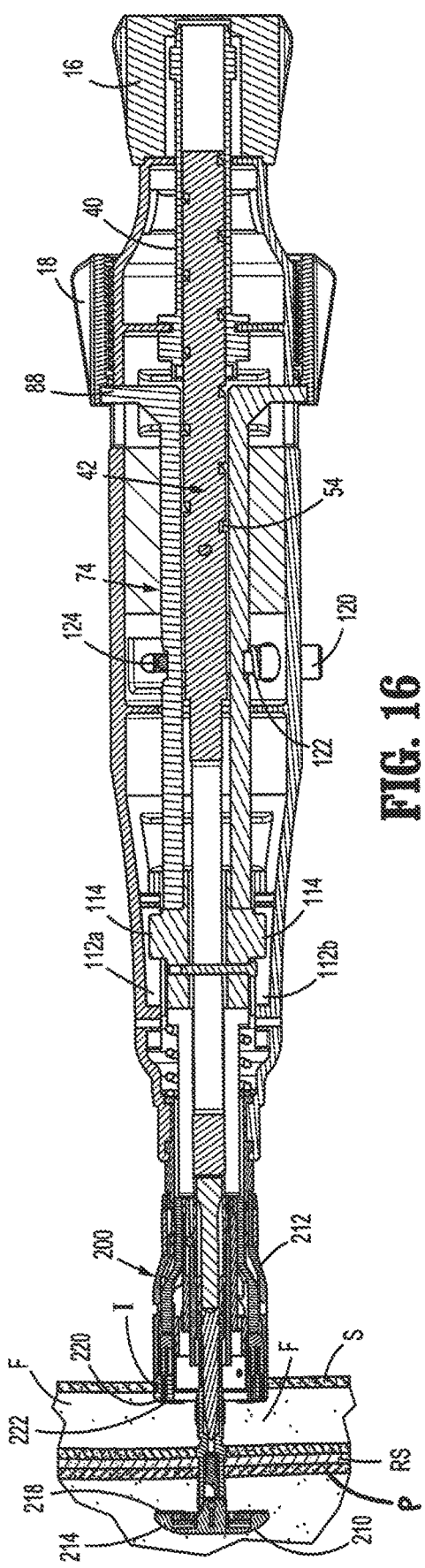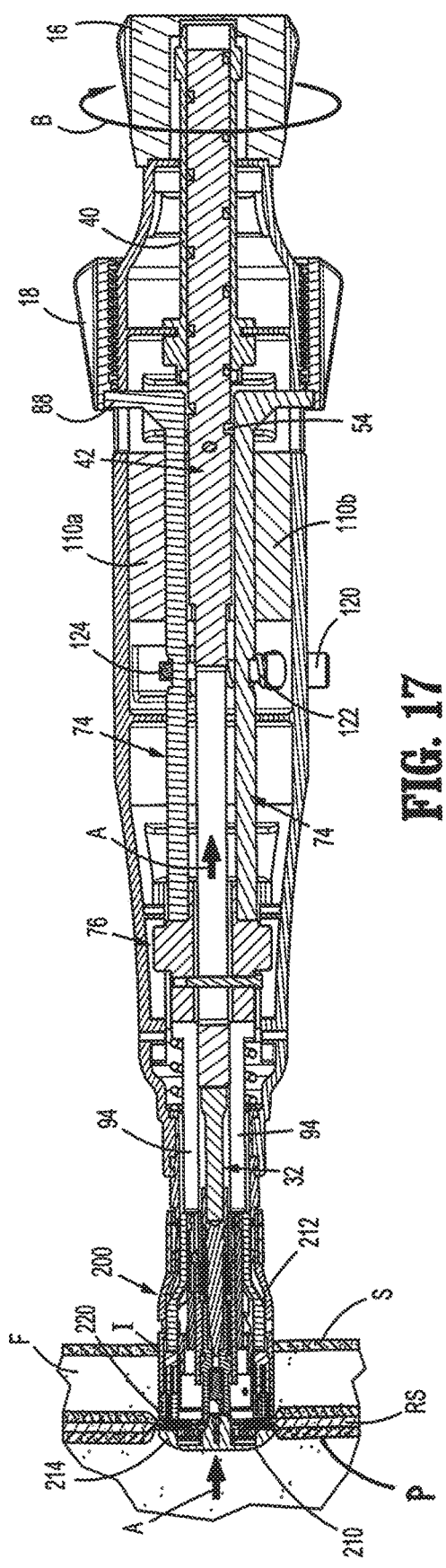

CIRCULAR STAPLING DEVICE AND METHOD OF USE

CROSS-REFERENCE TO RELATED APPLICATIONS

This application is a U.S. National Stage Application filed under 35 U.S.C. § 371(a) of International Patent Application Serial No. PCT/US2017/023353, filed Mar. 21, 2017, which claims the benefit of and priority to India Patent Application Serial No. 201741002959, filed Jan. 25, 2017, the entire disclosure of which is incorporated by reference herein.

BACKGROUND

1. Technical Description

The present disclosure is directed to circular stapling devices and methods of use and, more particularly, to circular stapling devices including a plurality of different tool assemblies configured for creating stomas.

2. Background of Related Art

During an ostomy procedure, a bisected portion of an intestine is secured to an exterior surface of the abdominal wall to provide internal access into the intestine for collecting fecal matter. The exteriorization of the intestine is called a stoma. Ostomy procedures include ileostomies and colostomies. In an ileostomy procedure, an end of the ileum (i.e., small intestine) is pulled through the abdominal wall and is flared outwardly and sutured to the skin, leaving a smooth, rounded, inside-out ileum as the stoma. In a colostomy procedure, an end or portion of the colon is pulled through the abdominal wall and flared outwardly and fastened (e.g., stitched) to the skin of the patient to form a stoma.

Ostomy surgery is sometimes performed on an emergency basis due to diverticulitis, trauma, radiation complications, volvulus, necrotic bowel, bowel perforation, etc. Children and adults alike may require an ostomy. An ostomy may only be temporary to allow for healing of the bowel or a decrease of inflammation at the surgical site. In some instances an ostomy may be permanent.

In known ostomy procedures, stomas are created by manually stitching the colon to the top layer of skin of the abdomen. Complications associated with manual suturing of the colon include suture granuloma, suture give away, and leaks. Other complications such as parastomal herniation which results from an improper incision or closure of the incision created in the anterior rectus sheath may require reoperation.

An improved device and method for creating a stoma to minimize complications resulting from stoma creation are desirable.

SUMMARY

One aspect of the present disclosure is directed to a method of creating a stoma including creating an abdominal incision accessing a rectus sheath of an abdominal wall; inserting a first tool assembly including an anvil assembly and a shell assembly having a staple cartridge through the abdominal incision; clamping the rectus sheath between the anvil assembly and the staple cartridge; and actuating the first tool assembly to create a circular incision through the rectus sheath.

In embodiments, actuating the first tool assembly includes advancing a knife of the shell assembly to form the circular incision through the rectus sheath.

In some embodiments, actuating the first tool assembly includes securing a buttress material to the rectus sheath to reinforce the circular incision.

In certain embodiments, the method further includes pulling a vessel portion through the circular incision and through the abdominal incision.

In embodiments, the vessel portion is selected from a colon, a small intestine, and a large intestine.

In some embodiments, the method further includes securing the vessel portion to the buttress material.

In certain embodiments, the method further includes inserting a second tool assembly through the abdominal incision and into the vessel portion, the second tool assembly including an anvil head supporting a stomal sleeve and a staple cartridge.

In embodiments, the method further includes clamping the stomal sleeve, the vessel portion, and a layer of skin between the anvil head and the staple cartridge of the second tool assembly.

In some embodiments, the method further includes actuating the second tool assembly to secure the stomal sleeve to the layer of skin and the vessel portion within the vessel portion.

In certain embodiments, actuating the second tool assembly includes separating a first end portion of the stomal sleeve from the anvil head with a knife of the second tool assembly.

In embodiments, the method further includes pulling the stomal sleeve through the vessel portion and the abdominal incision.

In some embodiments, the method further includes separating a second end portion of the stomal sleeve from the anvil head.

In certain embodiments, the step of separating the second end portion of the stomal sleeve from the anvil head includes manually cutting the second end portion of the stomal sleeve with a cutting device.

Another aspect of the present disclosure is directed to a kit including an actuator, a first tool assembly, and a second tool assembly. The actuator includes a housing and a distal coupling member. The first tool assembly is releasably couplable to the distal coupling member of the actuator and includes a first anvil assembly and a first shell assembly. The first shell assembly includes a staple cartridge having an annular array of staple pockets, each of the staple pockets supporting a staple. The second tool assembly is releasably couplable from the distal coupling member of the actuator and includes a second anvil assembly and a second shell assembly. The second anvil assembly includes an anvil head supporting a stomal sleeve.

In some embodiments, the anvil head of the first tool assembly supports a first buttress material and the staple cartridge of the first shell assembly supports a second buttress material.

Another aspect of the present disclosure is directed to a circular stapling device including an actuator having a housing, a clamping knob, and a firing knob. The firing knob and the clamping knob are rotatably supported on the housing. An approximation assembly is supported within the housing and includes a drive screw and an anvil retainer assembly secured to the drive screw. The anvil retainer assembly extends from a distal portion of the housing. The clamping knob is operably associated with the drive screw such that rotation of the clamping knob causes axial movement of the drive screw and the anvil retainer assembly in relation to the housing. A firing assembly is supported within the housing and includes at least one drive member and a pusher member engaged with a distal portion of the at least one drive member. The at least one drive member has a proximal portion positioned to be engaged by the firing knob. The firing knob is rotatably supported about the housing to cause axial movement of the firing knob in relation to the housing, wherein axial movement of the firing knob in relation to the housing causes axial movement of the at least one drive member and the pusher member in relation to the housing. A tool assembly is supported on a distal portion of the housing.

In some embodiments, the firing knob is threadably coupled to the housing.

In certain embodiments, the at least one drive member includes a transverse extension that extends through an opening in the housing, wherein the transverse extension is positioned to engage the firing knob.

In embodiments, the at least one drive member includes first and second drive members.

In some embodiments, the circular stapling device further includes a biasing member positioned to urge the pusher member and the at least one drive member proximally within the housing.

BRIEF DESCRIPTION OF THE DRAWINGS

Various embodiments of the presently disclosed circular stapling device and methods of use are described herein below with reference to the drawings, wherein:

FIG. 5 is a side perspective view of the actuator of the circular stapling device shown in FIG. 1 with a housing half-section removed;

FIG. 6 is a side perspective view of the actuator of the circular stapling device shown in FIG. 5 with additional internal components of the actuator removed;

FIG. 8 is a cross-sectional view taken along section line 8-8 of FIG. 7;

FIG. 9 is a cutaway view of a firing lock assembly of the circular stapling device shown in FIG. 8;

FIG. 16 is a side cross-sectional view of the circular stapling device shown in FIG. 1 with the first tool assembly in the unapproximated position within abdominal tissue;

FIG. 17 is a side cross-sectional view of the circular stapling device shown in FIG. 16 with the first tool assembly in an approximated position within abdominal tissue prior to firing of the circular stapling device;

DETAILED DESCRIPTION OF EMBODIMENTS

Figure 1:
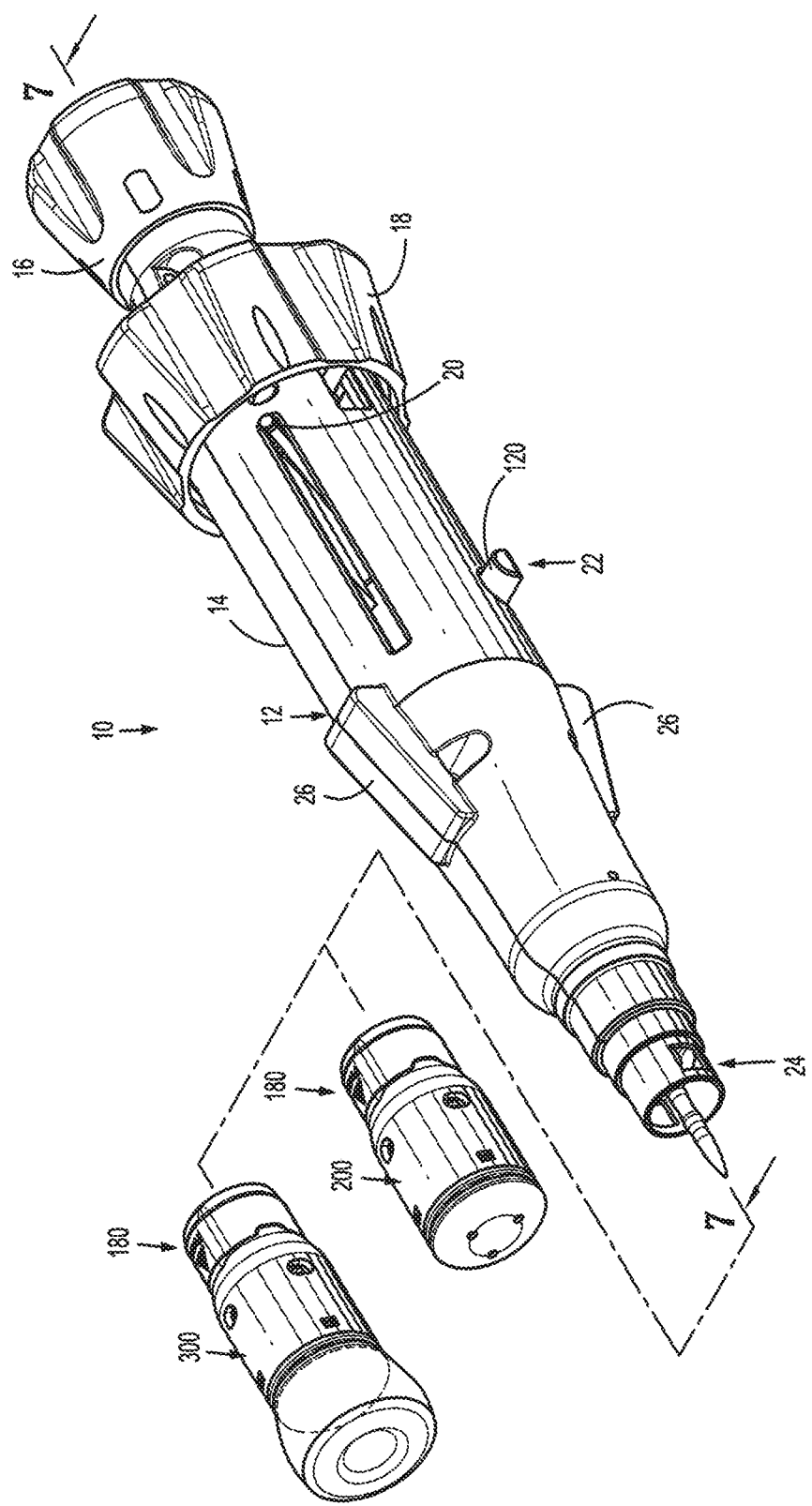
FIG. 1 is a side perspective view of an exemplary embodiment of the presently disclosed circular stapling device including the first and second tool assemblies with both tool assemblies with the tool assemblies separated from an actuator of the circular stapling device.

The presently disclosed circular stapling device and methods of use will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. In addition, the term clinician is used generally to refer to medical personnel including doctors, nurses, and support personnel.

FIG. 1 illustrates an exemplary embodiment of the presently disclosed circular stapling device shown generally as 10. The stapling device 10 includes an actuator 12 and first and second tool assemblies 200, 300, respectively. Although the stapling device 10 is shown to include two tool assemblies, it is noted that the actuator 12 of the circular stapling device 10 can be used with any one of a number of different types of tool assemblies including the first tool assembly 200, the second tool assembly 300, and other tool assemblies known in the art. The first and second tool assemblies 200, 300, respectively, are illustrated in this application to describe embodiments of a method of creating a stoma in abdominal tissue which is described in further detail below. This does not diminish the fact that the presently disclosed actuator 12 of the stapling device 10 may be used with a variety of tool assemblies to perform a variety of different surgical procedures. It is also envisioned that the presently disclosed tool assemblies and method can be actuated using a variety of manually and electro-mechanically driven actuators known in the art.

The actuator 12 of the stapling device 10 includes a housing 14 that functions as a grip, a clamping knob 16, a firing knob 18, an indicator member 20, and a firing lockout assembly 22. The housing 14 includes one or more protrusions 26 to enhance the grip ability of the housing 14. Although the protrusions 26 are illustrated as having a triangular configuration, it is envisioned that the configuration of the protrusions 26 and/or the housing 14 may be adapted to be more ergonomic and graspable. The housing 14 also supports a distal coupling member 24 that is configured to be releasably coupled to a proximal portion of one of the first and second tool assemblies 200, 300, respectively.

Figure 2:
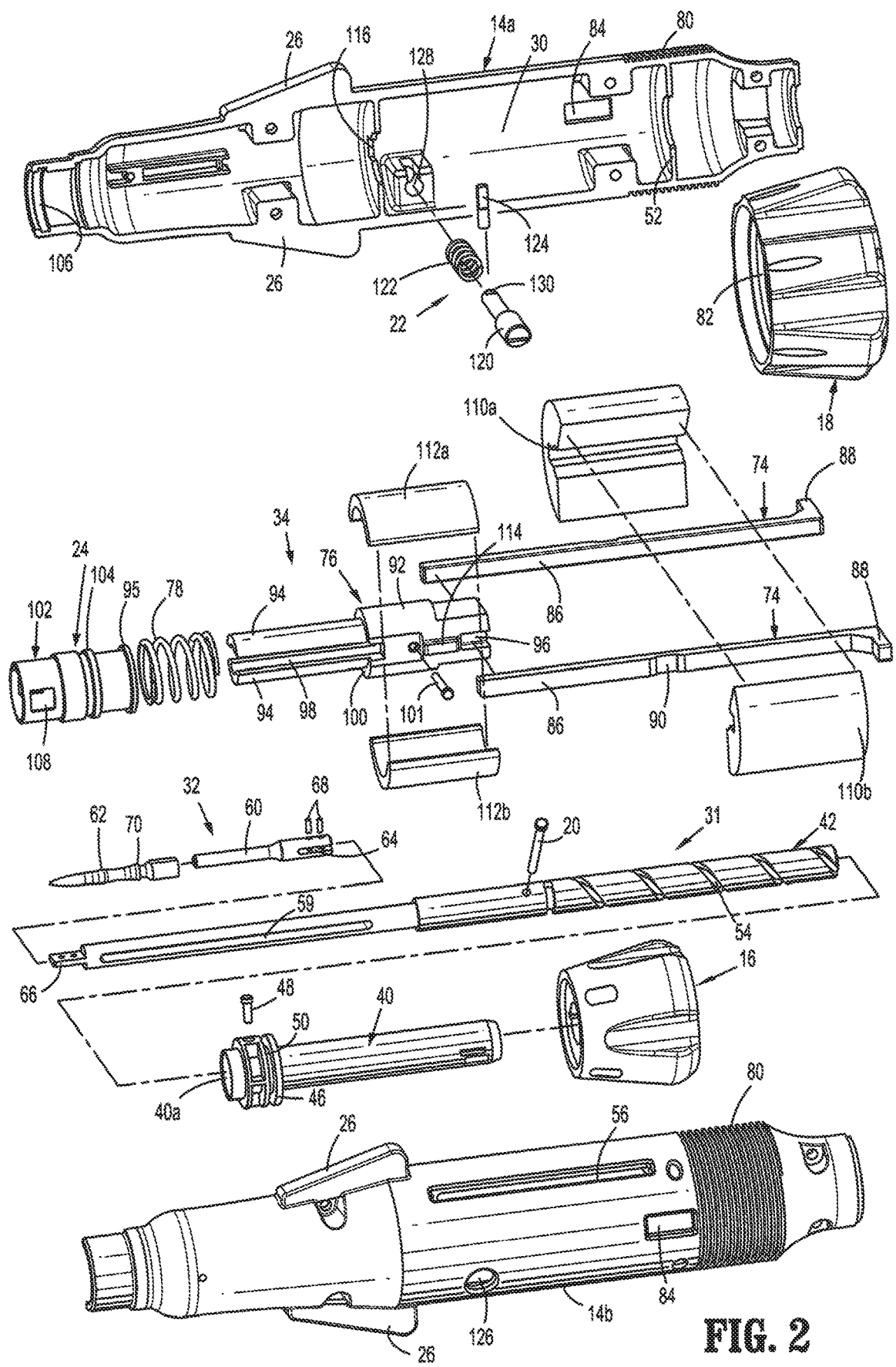
FIG. 2 is an exploded, side perspective view of the actuator of the circular stapling device shown in FIG. 1.

Referring to FIG. 2, in embodiments, the housing 14 is formed from molded half-sections 14a, 14b that can be secured together using any known fastening technique including, for example, welding, screws, adhesives, snap-fit connectors, etc. The molded half-sections 14a and 14b of the housing 14 define a cavity 30 that receives various components of the actuator 12 including an approximation assembly 31, a firing assembly 34, and a firing lockout assembly 36.

Figure 3:
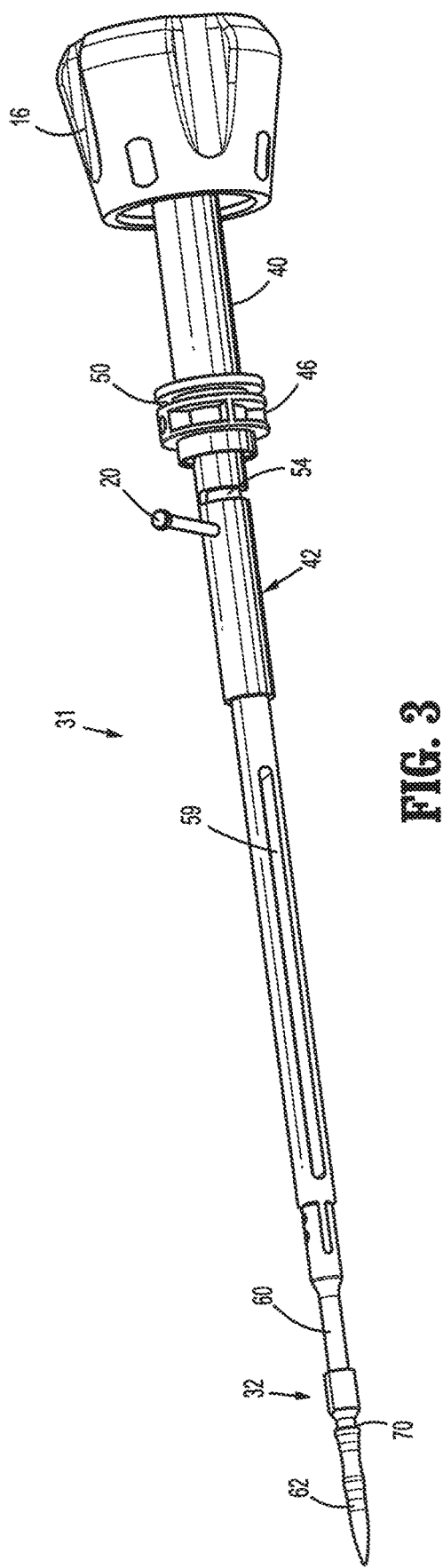
FIG. 3 is a side perspective view of the assembled screw assembly of the actuator of the circular stapling device shown in FIG. 2.

Referring also to FIG. 3, the approximation assembly 31 includes the clamping knob 16, a hollow sleeve 40, a drive screw 42, and an anvil retainer assembly 34. The clamping knob 16 is secured to a proximal portion of the hollow sleeve 40 such that rotation of the clamping knob 16 in relation to the housing 14 of the actuator 12 causes rotation of the hollow sleeve 40 within the housing 14. The hollow sleeve 40 defines a channel 40a (FIG. 2) and includes a distal portion that supports an annular collar 46. The annular collar 46 supports a pin 48 that extends through the collar 46 and into the channel 40a of the hollow sleeve 40. The annular collar 46 defines an annular slot 50 that receives a rib 52 (FIG. 6) formed on an interior surface of the housing half-sections 14a, 14b. The rib 52 fixes the axial position of the hollow sleeve 40 in relation to the housing 14.

The drive screw 42 includes a proximal portion that defines a helical channel 54 and is received within the channel 40a of the hollow sleeve 40. The helical channel 54 receives the pin 48. When the clamping knob 16 is rotated to rotate the hollow sleeve 40 about the drive screw 42, the pin 48 moves within the helical channel 54 of the drive screw 42 to cause axial movement of the drive screw 42 within the hollow sleeve 40.

The indicator member 20 is secured to a central portion of the drive screw 42 and extends through an elongated slot 56 in the housing half-section 14b. The indicator member 20 is movable within the elongated slot 56 to provide an indication to a clinician of the axial location of the drive screw 42 within housing 14. By identifying the axial location of the drive screw 42 within the housing 14, the clinician can identify the degree of approximation of a tool assembly secured to the distal coupling member 24, e.g., the tool assembly 200 or 300. The indicator member 20 and elongated slot 56 also prevent rotation of the drive screw 42 within the housing 14 to restrict the drive screw 42 to axial movement within the housing 14.

Figure 7:
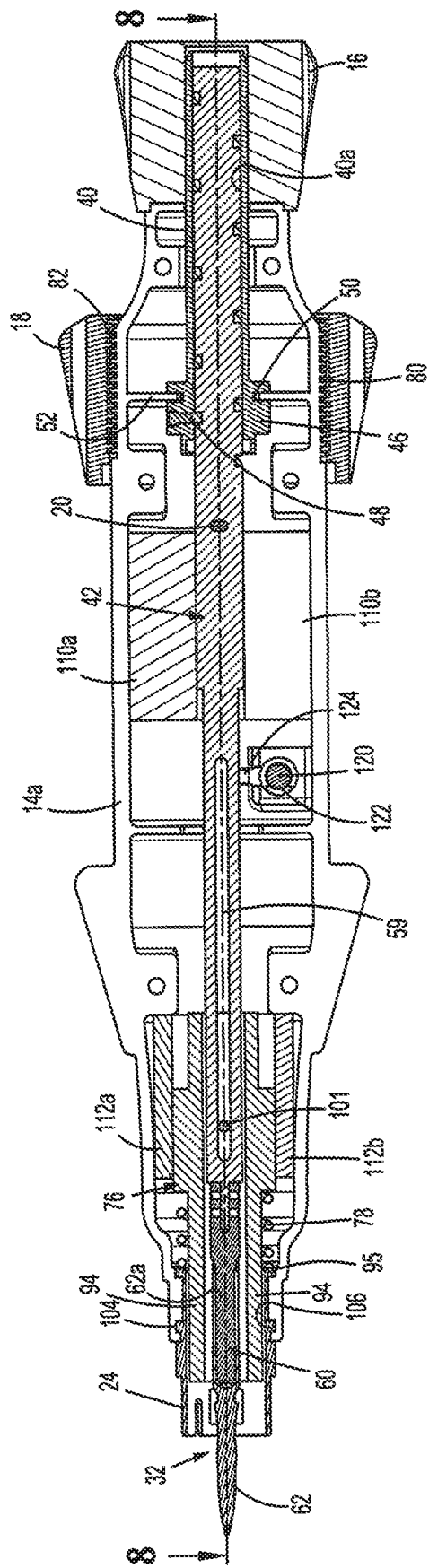
FIG. 7 is a side cross-sectional view of the actuator of the circular stapling device shown in FIG. 2.

A distal portion of the drive screw 42 defines an elongated slot 59 (FIG. 2). A distal end of the distal portion of the drive screw 42 is secured to a proximal portion of the anvil retainer assembly 32. In embodiments, the anvil retainer assembly 32 includes a base member 60 and a trocar member 62. The base member 60 defines a slot 64 that receives a distal extension 66 formed on the drive screw 42 such that the base member 60 can be secured to the drive screw 42 using screws or rivets 68. The trocar member 62 of the anvil retainer assembly 32 defines a proximal opening 62a (FIG. 7) that receives a distal portion of the base member 60 to secure the base member 60 to the trocar member 62. The distal portion of the base member 60 can be secured within the proximal opening of the trocar member 62 using any known fastening technique including welding, crimping, or the like. A distal portion of the trocar member 62 is tapered to facilitate passage of the trocar member 62 through tissue. The trocar member 62 also defines an annular rib 70 to facilitate coupling of the trocar member 62 to an anvil assembly of a tool assembly, e.g., tool assemblies 200 or 300.

In use, when the clamping knob 16 is manually rotated by a clinician, engagement of the pin 48 with the walls defining the helical channel 54 of the drive screw 42 causes the drive screw 42 to move axially within the channel 40a of the hollow sleeve 40. As the drive screw 42 moves axially within the channel 40a of the hollow sleeve 40, the anvil retainer assembly 32 moves axially with the drive screw 42 in relation to the housing 14. As discussed above, an anvil assembly of the tool assembly 200, 300 is secured to the trocar member 62 of the anvil retainer assembly 32 such that axial movement of the trocar member 62 causes axial movement of the anvil assembly.

Figure 4:
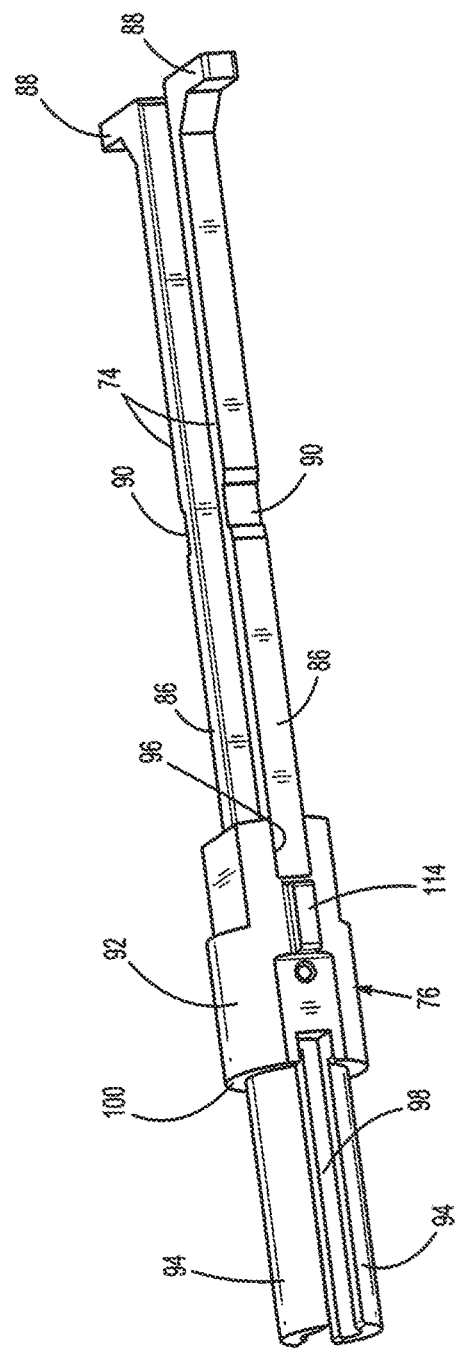
FIG. 4 is a side view of the cartridge shaft assembly of the actuator of the circular stapling device shown in FIG. 9.

Referring to FIGS. 2 and 4, the firing assembly 34 includes the firing knob 18, a pair of drive members 74, a pusher member 76, and a biasing member 78. The firing knob 18 is supported about a proximal portion of the housing 14 for axial movement. In embodiments, the proximal portion of the housing 14, including housing half-sections 14a, 14b, includes screw threads 80 that mate with internal threads 82 (FIG. 2) formed on an inner wall of the firing knob 18 such that rotation of the firing knob 18 about the housing 14 causes axial movement of the firing knob 18 about the housing 14. It is envisioned that other structures that facilitate axial movement of the firing knob 18 in a controlled manner along the housing 14 can be substituted for the threaded arrangement shown.

Each of the housing half-sections 14a and 14b defines an opening 84 (FIG. 2). Each of the drive members 74 includes an elongated leg 86, a transverse extension 88 positioned on a proximal portion of the elongated leg 86, and a notch 90. Each of the transverse extensions 88 extends through a respective one of the openings 84 and is positioned to engage the firing knob 18 such that axial advancement of the firing knob 18 along the housing 14 causes corresponding axial movement of the drive members 74 within the housing 14.

The pusher member 76 includes a body 92 and a pair of fingers 94 that extend distally from the body 92. In embodiments, the body 92 defines a pair of diametrically spaced cutouts 96 (FIG. 2) that receive the distal ends of the elongated legs 86 of the drive members 74 such that axial advancement of the drive members 74 causes axial movement of the pusher member 76 within the housing 14. The fingers 94 are dimensioned to extend from the distal portion of the housing 14, through the distal coupling member 24, and into the tool assembly, e.g., 200, 300. The fingers 94 and slots 98 defined between the fingers 94 facilitate movement of the fingers 94 into and within a shell assembly of the tool assembly, e.g., tool assembly 200, 300, to eject staples from the tool assembly.

Referring also to FIGS. 5-9, the body 92 of the pusher member 76 includes a distal face that defines a shoulder 100 that is positioned about the fingers 94. The biasing member 78, which can be in the form of a torsion spring, is positioned between on annular flange 95 formed about the distal coupling member 24 and the shoulder 100 of the body 92 of the pusher member 76 to urge the pusher member 76 towards a retracted position within the housing 14.

In use, when the firing knob 18 is rotated and advanced axially about the housing 14, the firing knob 18 engages the transverse extensions 88 of the drive members 74 to advance the drive members 74 within the housing 14. As the drive members 74 are advanced, the distal ends of the drive members 74 which are received within the cutouts 96 of the pusher member 76 advance the pusher member 76 within the housing 14 against the bias of the biasing member 78. As the pusher member 76 is advanced, the fingers 94 of the pusher member 76 are extended further distally from the distal end of the housing 14 and the distal coupling member 24 into a shell assembly of a tool assembly, e.g., 200, 300, to eject staples from the tool assembly.

When the firing knob 18 is moved proximally along the housing 14 towards a retracted position, the biasing member 78 urges the pusher member 76 and the drive members 74 back to their retracted positions. Alternately, the firing knob 18 could be coupled to the drive members 74 and the drive members 74 could be secured to the pusher member 76 such that proximal movement of the firing knob 18 would return the drive members 74 and the pusher member 76 to their retracted position.

The distal coupling member 24 includes a cylindrical body 102 having an annular flange 104. The annular flange 104 is received within an annular slot 106 (FIG. 2) formed in the housing half-sections of the housing 14 to axially secure the distal coupling member 24 on the distal end of the housing 14 between the housing half-sections 14a and 14b. The body 102 defines a pair of diametrically opposed openings 108 that receive a coupling member described below to secure the tool assembly to the distal coupling member 24.

The distal portion of the drive member 42 extends through the pusher member 76. A pin 101 extends through the body 92 of the pusher member 76 and through the elongated slot 59 of the drive screw 42 to prevent rotation of the drive screw 42 within the pusher member 76.

The housing supports a first pair of spacers 110a, 110b that are positioned within the cavity 30 defined by the housing 14 about the drive members 74 to maintain the position of the drive members 74 within the cavity 30. In addition, the housing 18 supports a second pair of spacers 112a, 112b that are positioned about the body 92 of the pusher member 76 to maintain the position of the pusher member within the housing 14. The body 92 of the pusher member 76 includes wings 114 that extend between the spacers 112a, 112b and are received in cutouts 116 (FIG. 2) formed in the housing half-sections 14a, 14b to prevent the pusher member 76 from rotating within the housing 14.

The firing lockout assembly 22 includes an actuator 120, a biasing member 122, and a stop member 124. The actuator 120 extends through an opening 126 (FIG. 2) formed in the housing half-section 14b (FIG. 2) and into a recess 128 defined within the housing half-section 14a (FIG. 2). The actuator 120 defines an opening 130 (FIG. 2) that receives the stop member 124 such that the stop member 124 extends along an axis substantially transverse to the axis defined by the actuator 120. The biasing member 122, which may be in the form of a torsion spring, is positioned about the actuator 120 between an actuator head 120a to urge the actuator 120 outwardly from the hole 126 formed in the housing 14 such that the stop member 124 is received within the notch 90 of the elongated leg 86 of one of the drive members 74. The stop member 124 defines a flat 124a (FIG. 9). The flat 124a engages a surface defining the notch 90 to prevent axial movement of the drive member 74 in relation to the housing 14 when the stop member 124 is positioned within the notch 90. The actuator 120 can be pressed inwardly through the opening 126 in housing half-section 14b to lift the stop member 124 from the notch 90 to facilitate advancement of the drive members 74.

Figure 10:
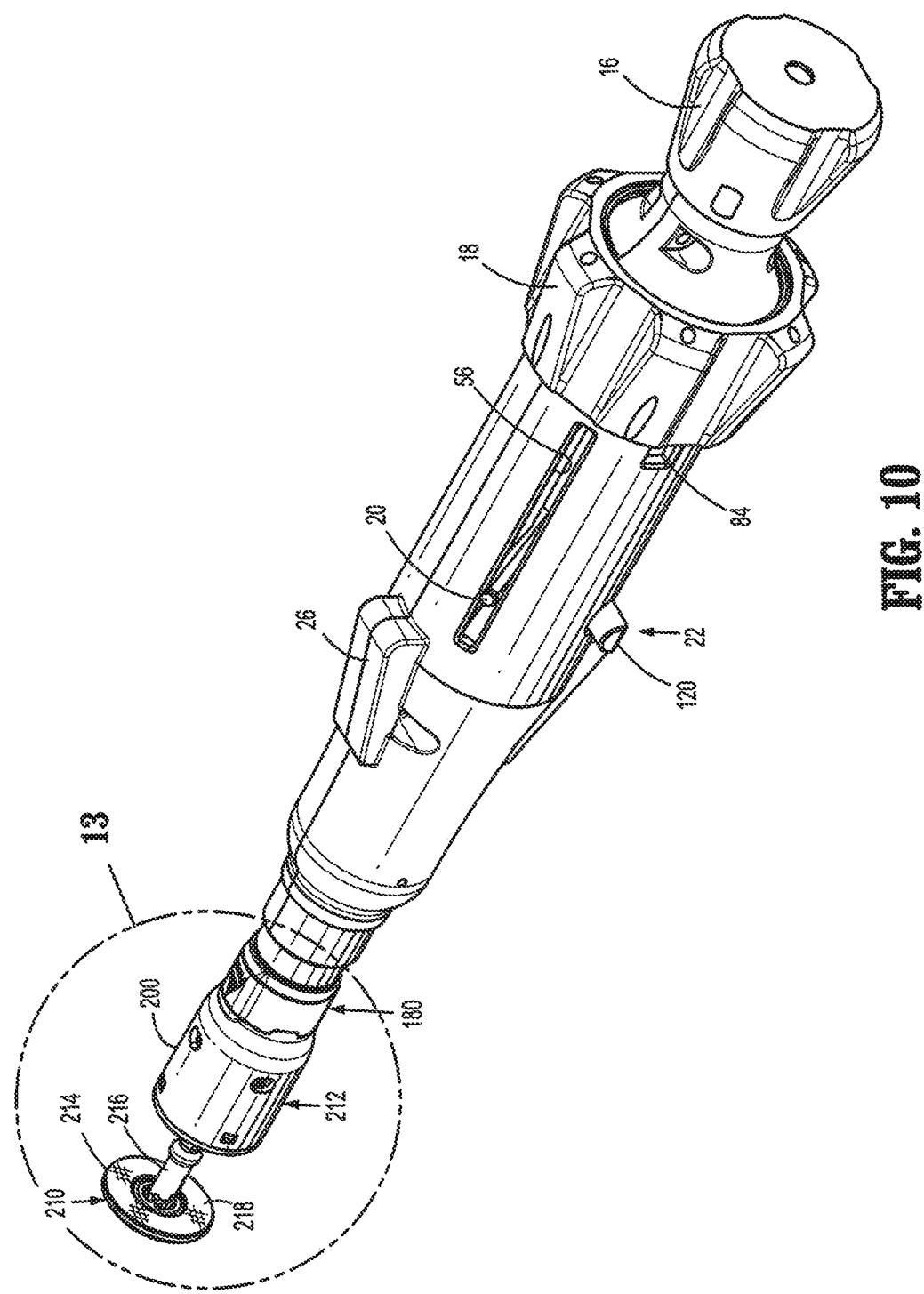
FIG. 10 is a side perspective view of the circular stapling device shown in FIG. 1 with the first tool assembly in an unapproximated position attached to the actuator.
Figure 11:
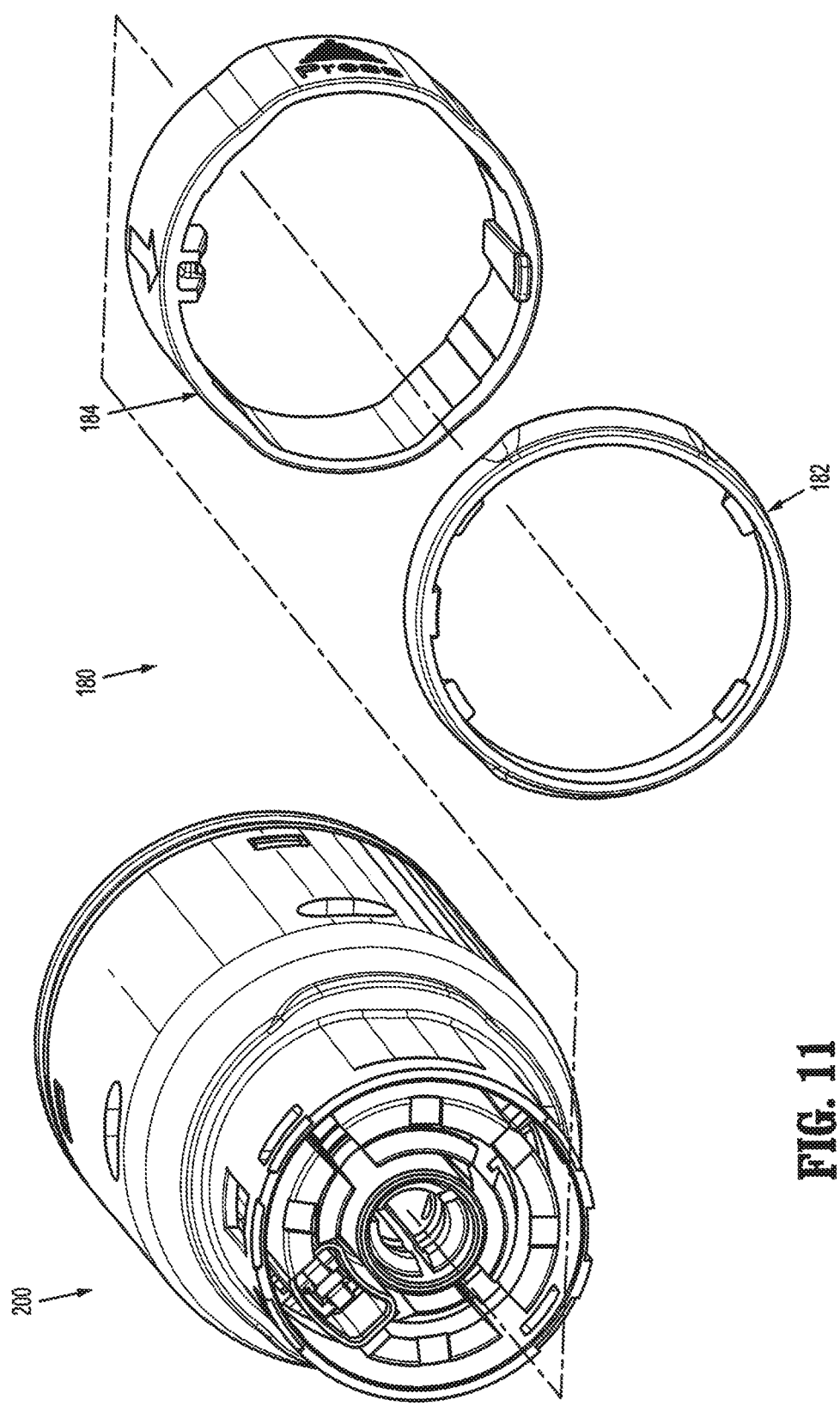
FIG. 11 is a side perspective view of the first tool assembly shown in FIG. 1 with a coupling assembly separated from a shell assembly of the first tool assembly.

Referring to FIGS. 10 and 11, as discussed above the tool assemblies 200 and 300 (FIG. 1) can be releasably coupled to the distal coupling member 24 of the housing 14 of the actuator 12. Both of the anvil assemblies 200, 300 include a retainer assembly 180 including a retainer ring 182 and a locking collar 184. The retainer assembly 180 releasably couples a respective tool assembly to the distal coupling member 24 of the actuator 12. The structure and operation of the retainer assembly 180 are described in further detail in U.S. Publication No. 2016/0192939 which is incorporated herein by reference in its entirety. Since the retainer assembly 180 is not the focus of this application, the retainer assembly 180 will not be described in further detail herein. U.S. Publication Nos. 2016/0157856, 2016/0192934, and 2016/0192938, and U.S. application Ser. No. 15/205,169 disclose different embodiments of retainer assemblies for releasably coupling a tool assembly to an actuator of a surgical stapling device and are also incorporated herein in their entirety by reference.

Figure 12:
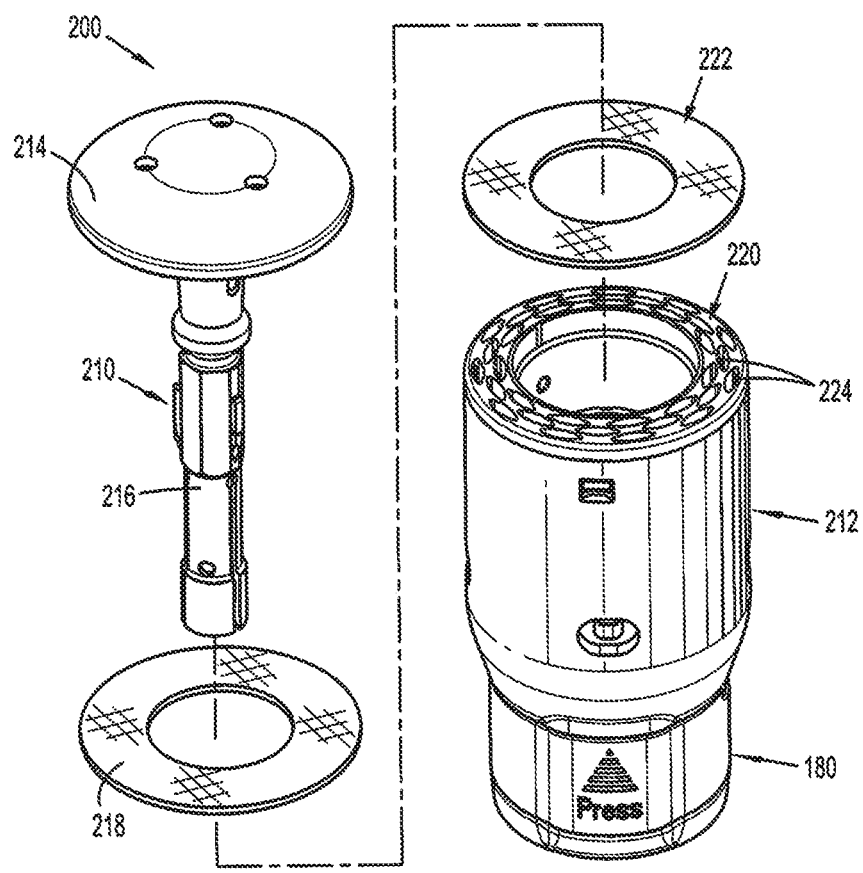
FIG. 12 is a side perspective, exploded view of the first tool assembly shown in FIG. 10.
Figure 13:
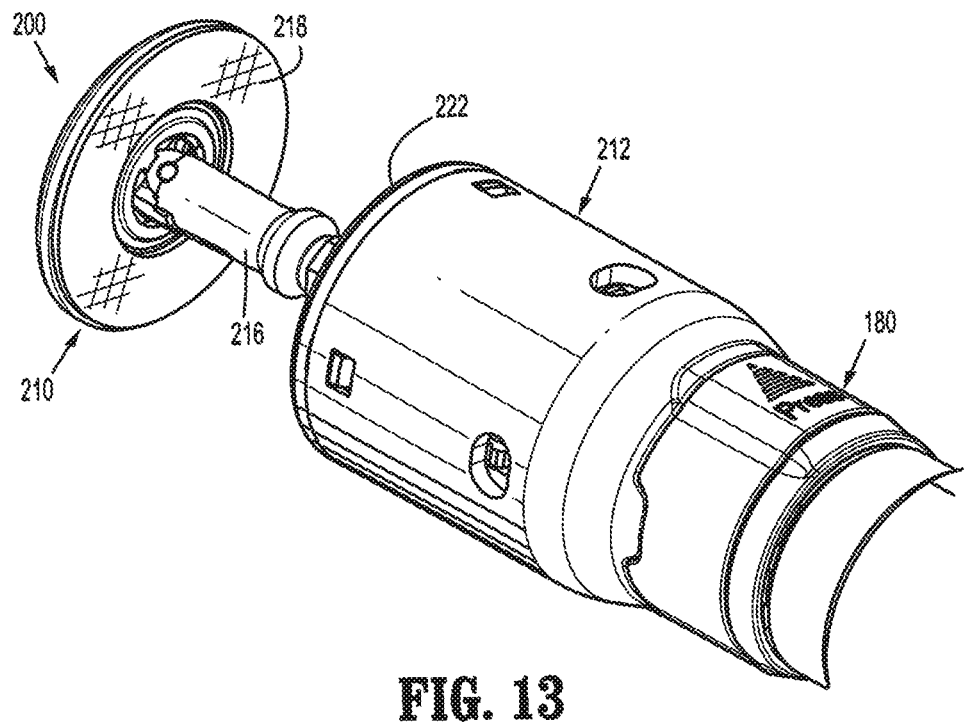
FIG. 13 is an enlarged view of the indicated area of detail shown in FIG. 10.

Referring to FIGS. 12 and 13, the first tool assembly 200 includes an anvil assembly 210, a shell assembly 212, and the retainer assembly 180. The anvil assembly 210 includes an anvil head 214 defining a tissue contact surface (not shown), a center rod 216, and a first buttress material 218 that is supported on the tissue contact surface of the anvil head 214. The center rod 216 is configured to be releasably coupled to the trocar member 62 of the anvil retainer assembly 32 (FIG. 5) such that movement of the trocar member 62 between retracted and advanced positions causes movement of the anvil assembly 210 in relation to the shell assembly 212 between spaced and approximated positions. Although not shown in detail, the anvil head 214 can be pivotally secured to the center rod 216 and movable from an operative position shown in FIG. 13 to a tilted position. U.S. Pat. No. 8,540,132 discloses an anvil assembly having a tiltable anvil head and is incorporated herein by reference in its entirety.

The shell assembly 212 includes a staple cartridge 220 and a second buttress material 222. The staple cartridge 220 includes a tissue contact surface 220a that defines a plurality of staple pockets 224 arranged in annular arrays. The second buttress material 222 is secured to the tissue contact surface 220a of the staple cartridge 220. Each staple pocket 224 receives a staple (not shown). Although not described in detail, the shell assembly 212 includes a staple pusher and an knife "K" (FIG. 22) which can be advanced in response to advancement of the pusher member 76 (FIG. 2) to eject staples from the staple cartridge 220 and cut tissue. U.S. Pat. No. 7,364,060 ("the '060 patent") discloses the inner components of a known shell assembly and is incorporated herein by reference. Alternately, only one of the anvil head 214 and the staple cartridge 220 can include a buttress material.

Figure 14:
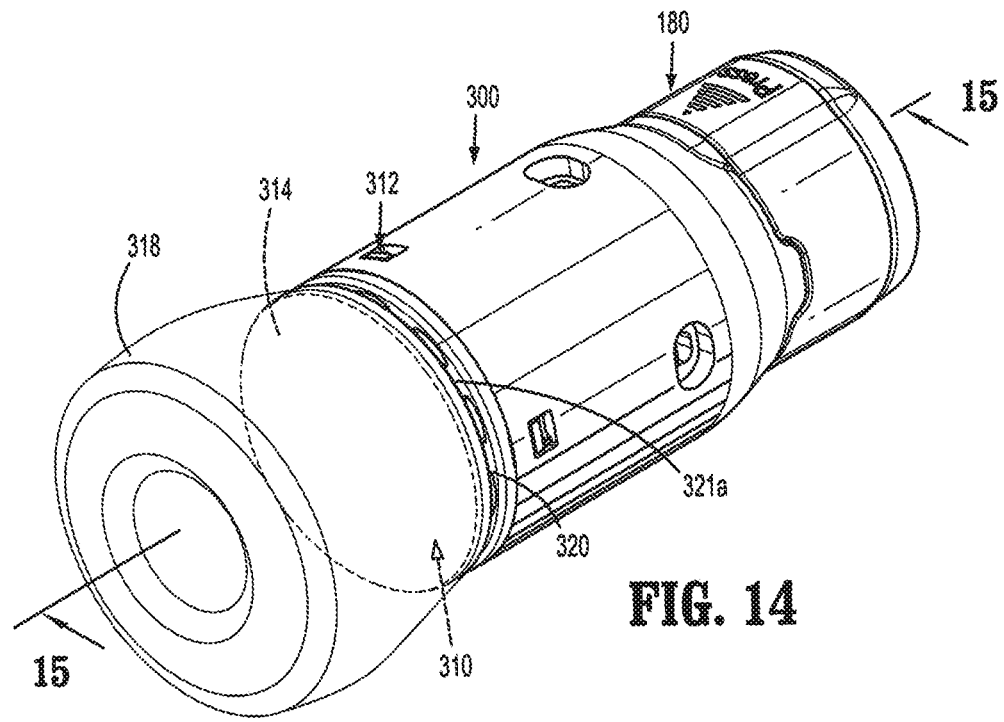
FIG. 14 is a side perspective view of the second tool assembly shown in FIG. 1.
Figure 15:
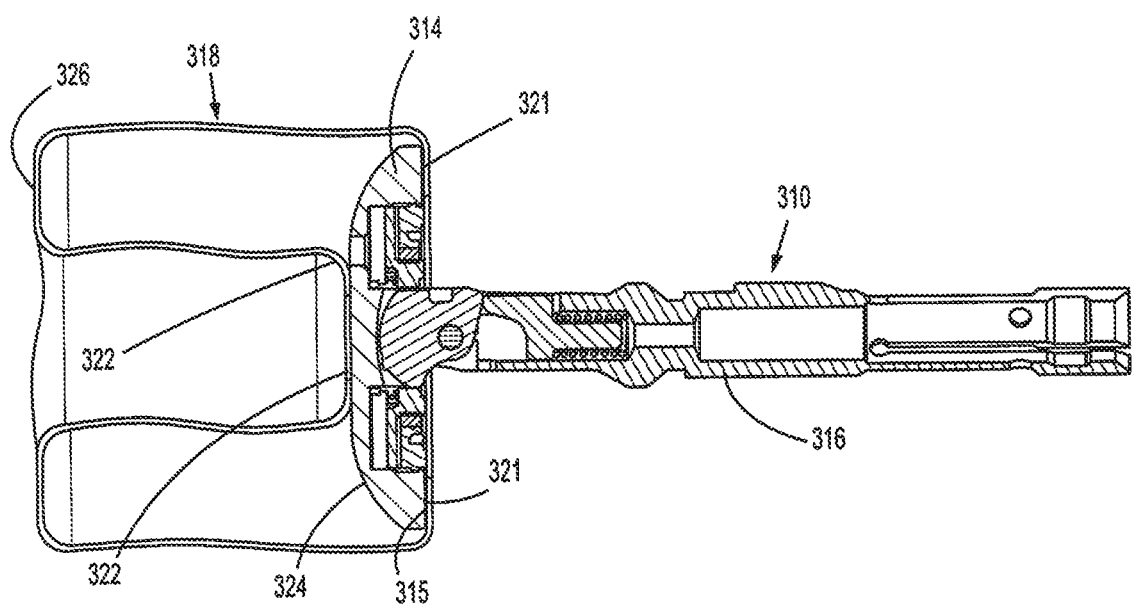
FIG. 15 is a cross-sectional view taken along section line 15-15 of FIG. 14.

Referring to FIGS. 14 and 15, the second tool assembly 300 includes an anvil assembly 310, a shell assembly 312, and the retainer assembly 180. The anvil assembly 310 includes an anvil head 314 defining a tissue contact surface 315, a center rod 316, and a stomal sleeve 318 that is supported on the anvil head 314. The tissue contact surface 315 defines staple deforming pockets (not shown). The center rod 316 is configured to be releasably coupled to the trocar member 62 of the anvil retainer assembly 32 (FIG. 5) such that movement of the trocar member 62 between retracted and advanced positions causes movement of the anvil assembly 310 in relation to the shell assembly 312 between spaced and approximated positions.

The stomal sleeve 318 has a tubular configuration and may be formed from a biocompatible, non-degradable, pliable material, e.g., a polymeric material. In embodiments, the stomal sleeve 318 has a first end portion 321 that is secured to the tissue contact surface 315 of the anvil head 314 at a location radially inwardly of the annular array of staple deforming pockets 319 and a second end portion 322 that is secured to the distally facing surface 324 of the anvil head 314 such that a central portion 326 of the stomal sleeve 318 is positioned distally of the second end portion 322 of the stomal sleeve 318. The end portions 321, 322 of the stomal sleeve 318 can be secured to the anvil head 314 using adhesives or the like. In embodiments, the first end portion 321 of the stomal sleeve 318 defines an opening 330 (FIG. 3A) and the second end portion 322 is closed. It is envisioned that both of the first and second end portions 321, 322 of the stomal sleeve 318 can initially define an opening or be closed.

The shell assembly 312 includes a staple cartridge 320 that includes a tissue contact surface 321a that defines a plurality of staple pockets 324 arranged in annular arrays. Although not described in detail, the shell assembly 312 includes a staple pusher 382 and an annular knife "K" (FIG. 22) which can be advanced in response to advancement of the pusher member 76 (FIG. 2) to eject staples 380 from the staple cartridge 320 and cut tissue. The '060 patent discloses the inner components of a known shell assembly and is incorporated herein by reference.

The surgical stapling device 10 including the actuator 12 and the first and second tool assemblies 200, 300 are particularly suited for performing ostomy procedures. Ostomy procedures include ileostomies and colostomies. In an ileostomy procedure, an end of the ileum (i.e., small intestine) is pulled through the abdominal wall and is flared outwardly and sutured to the skin, leaving a smooth, rounded, inside-out ileum as the stoma. In a colostomy procedure, an end or portion of the colon is pulled through the abdominal wall and flared outwardly and fastened (e.g., stitched) to the skin of the patient to form a stoma.

Referring to FIGS. 16-22, during an ostomy procedure using the surgical stapling device 10, an incision "I" is created in the abdominal wall and fat and tissue "F" located between the rectus sheath "RS" and the outer layer of skin "S" is removed through the incision "I" to allow the skin to be pulled close for suturing. The first tool assembly 200 is secured to the actuator 12 (FIG. 1) and the tool assembly 200 is inserted through the incision "I" with the anvil assembly 210 spaced in relation to the staple cartridge 220 of the shell assembly 212. The tool assembly 200 is positioned with the anvil head 214 on one side of the rectus sheath "RS" and the staple cartridge 220 is positioned on the other side of the rectus sheath "RS" (FIG. 16). In some embodiments, the anvil head 214 is positioned on one side of the peritoneum "P" and the posterior rectus sheath "RS". When the tool assembly 200 is properly positioned adjacent the peritoneum "P" and the rectus sheath "RS", the anvil head 214 is drawn towards the staple cartridge 220 in the direction indicated by arrow "A" in FIG. 17 by rotating the clamping knob 16 in the direction indicated by arrow "B". As the clamping knob 16 is rotated, the drive screw 42 is drawn into the hollow sleeve 40 to draw the anvil retainer assembly 32 into the shell assembly 212 and draw the anvil head 214 towards the staple cartridge 220 to clamp the peritoneum "P" and the rectus sheath "RS" and other tissue between the anvil head 214 and the staple cartridge 220 (FIG. 17).

Figure 18:
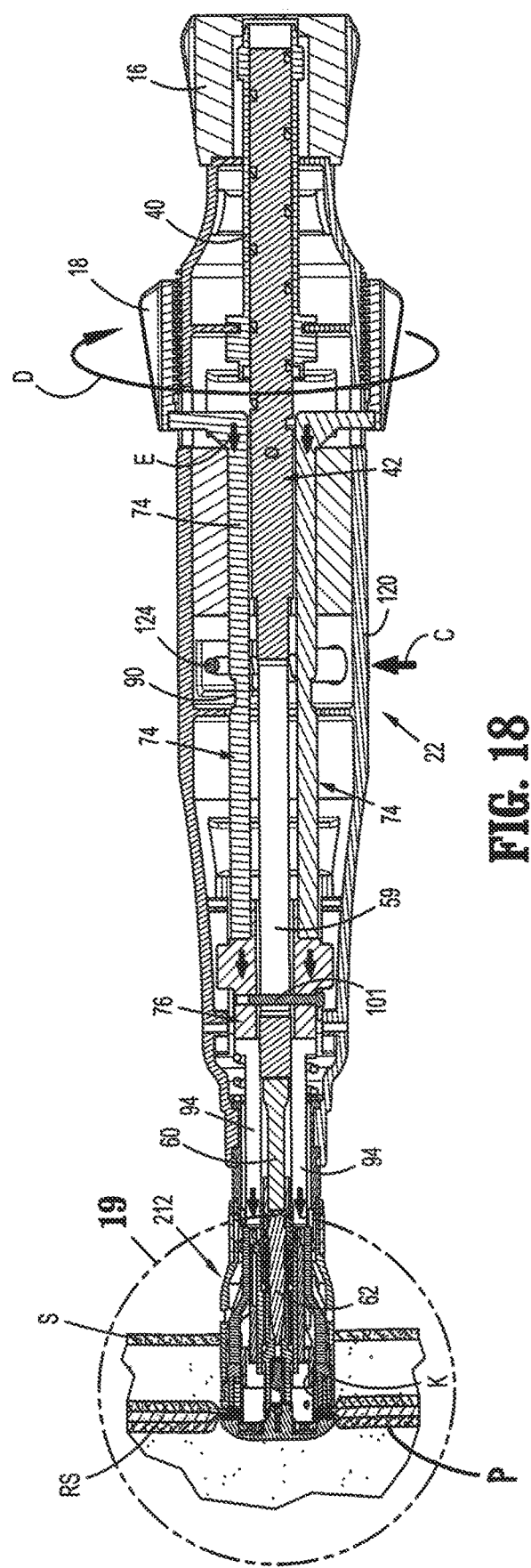
FIG. 18 is a side cross-sectional view of the circular stapling device shown in FIG. 17 with the first tool assembly in an approximated position within abdominal tissue as the circular stapling device is being fired.
Figure 19:
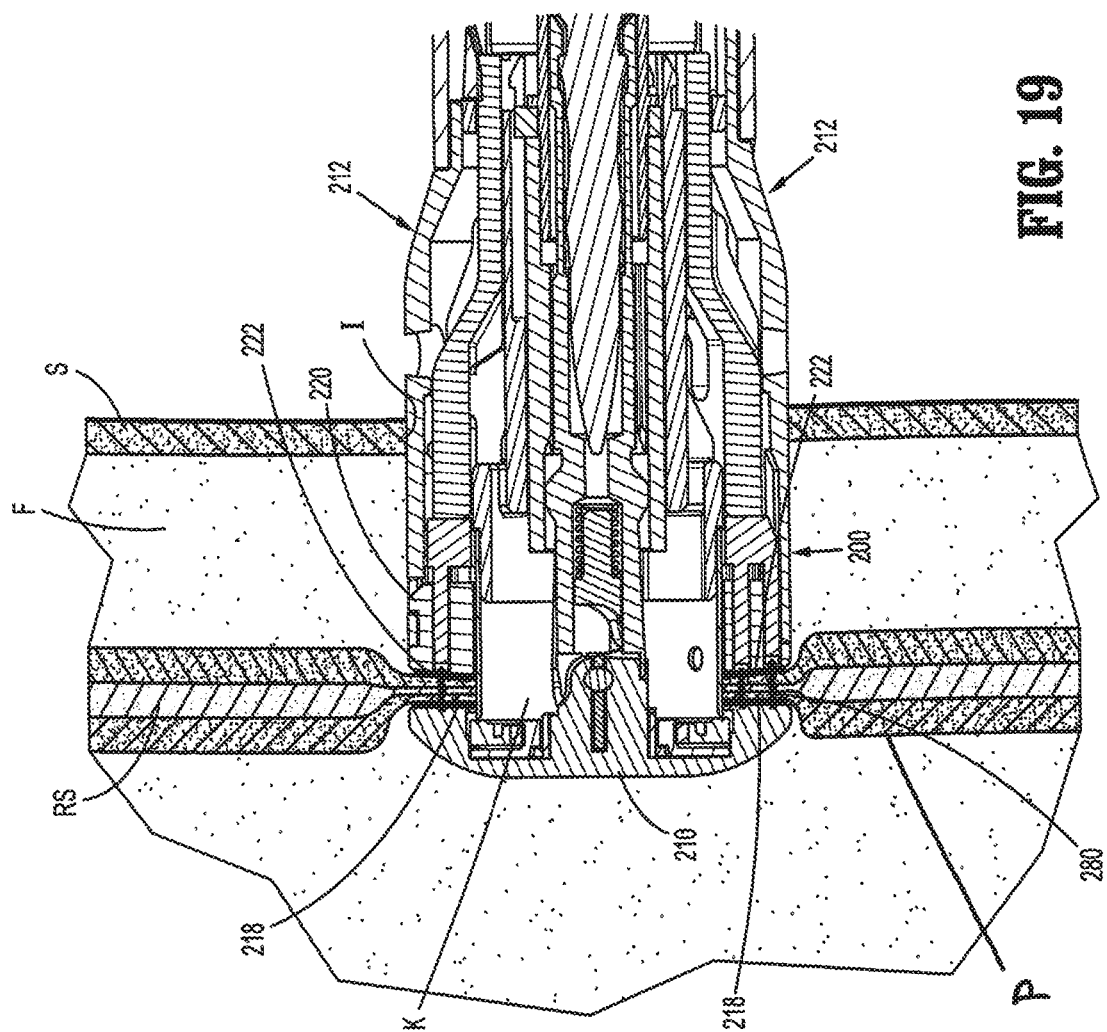
FIG. 19 is an enlarged view of the indicated area of detail shown in FIG. 18.
Figure 20:
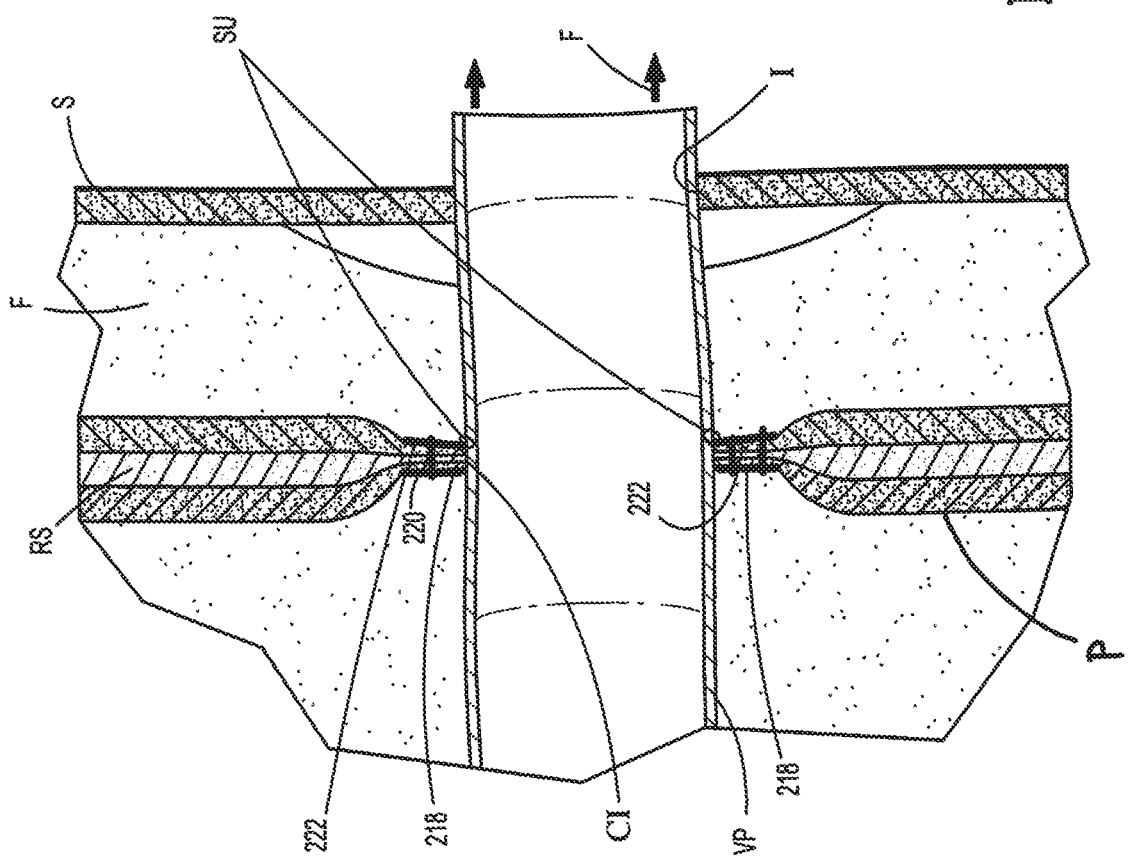
FIG. 20 is a side view of the abdominal tissue after the first tool assembly has been fired, the circular stapling device is removed from the abdominal tissue, and a portion of the bowel has been pulled through an opening formed in the abdominal tissue by the first tool assembly to form a stoma.

Referring to FIGS. 18-20, after the peritoneum "P" and the rectus sheath "RS" is clamped between the anvil head 214 and the staple cartridge 220, the stapling device 10 is fired to create a reinforced circular incision "CI" through the rectus sheath "RS". In order to fire the stapling device 10, the firing lockout assembly 22 must be actuated to remove the stop member 124 (FIG. 18) from within the notch 90 of one of the drive members 74. In order to actuate the firing lockout assembly 22, the actuator 120 is pressed inwardly in the direction indicated by arrow "C" in FIG. 18 against the urging of the biasing member 122 (FIG. 2) to lift the stop member 124 from within the notch 90. When the stop member 124 is lifted from the notch 90, the firing knob 18 can be rotated in the direction indicated by arrow "D" in FIG. 18 to advance the drive members 74 in the direction indicated by arrow "E".

As discussed above, advancement of the drive members 74 advances the pusher member 76 distally within the housing 14 to move the fingers 94 of the pusher member 76 into the shell assembly 212 to eject an annular array of staples 280 (FIG. 20) from the staple cartridge 220 and advance an annular knife "K" to cut tissue. When the staples 280 are ejected from the staple cartridge 220, the staples 280 pass through the second buttress material 222, the rectus sheath "RS", and the first buttress material 218 such that the first and second buttress materials 218 and 222 are stapled to opposite sides of the peritoneum "P" and the rectus sheath "RS". In addition, the knife "K" of the shell assembly 212 forms a circular incision through the peritoneum "P" and the rectus sheath "RS" that is bound by the first and second buttress materials. 218, 222. The use of the buttress materials 218 and 222 reinforces the circular incision "CI" and minimizes the risk of parastomal herniation. Alternately, the first tool assembly 200 need not include buttress materials such that the staples 280 provide reinforcement for the circular incision "CI".

Referring to FIG. 20, after the circular incision "CI" is formed through the peritoneum "P" and the rectus sheath "RS", a vessel portion "VP", e.g., colon, small intestine, large intestine, is pulled in the direction indicated by arrow "F" through the circular incision "CI" and through the incision "I". Thereafter, the vessel portion "VP" is sutured using a suture "SU" to the first and second buttress materials 218, 222.

Figure 21:
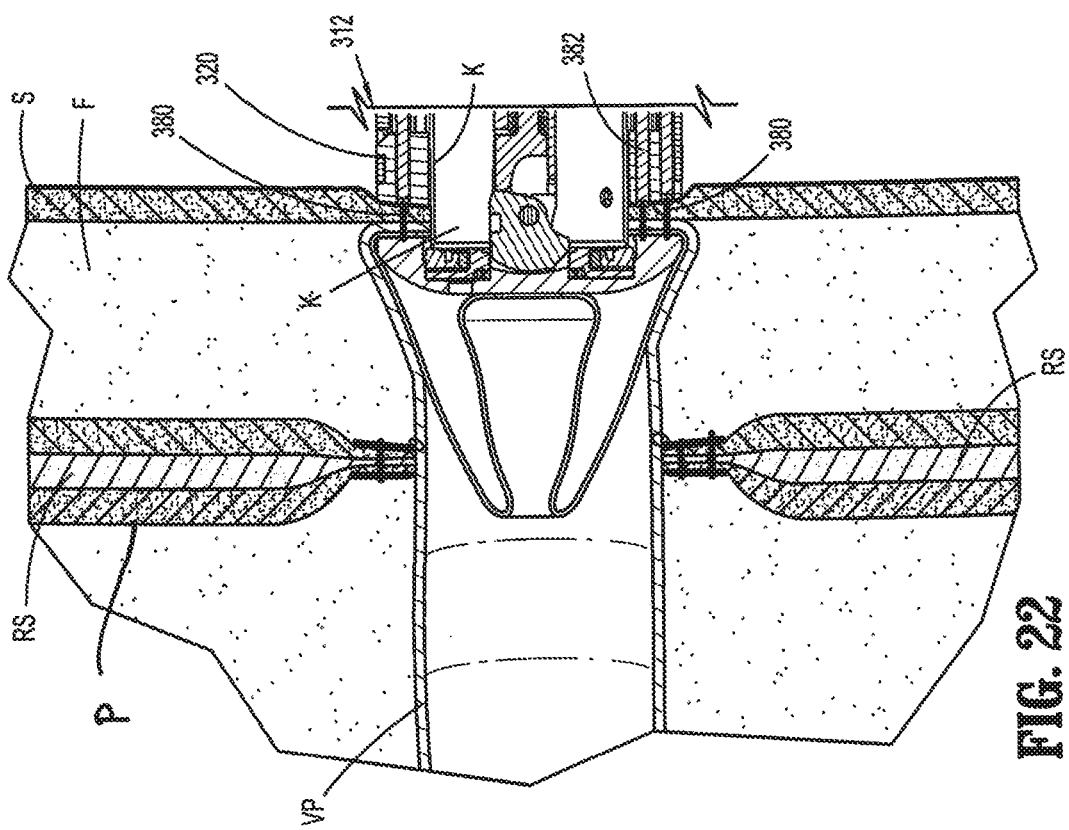
FIG. 21 is a side cross-sectional view of the actuator of the circular stapling device shown in FIG. 1 attached to the second tool assembly prior to movement of the second tool assembly to the approximated position with the second tool assembly positioned within the stoma.

Referring to FIG. 21, after the vessel portion "VP" is pulled through the incision "I" in the skin "S", the second tool assembly 300 is secured to the actuator 12 (FIG. 1) and the anvil head 314 of the tool assembly 300 of the surgical stapling device 10 is inserted through the vessel portion "VP" and the incision "I" with the staple cartridge 320 and anvil head 314 in an unapproximated position. In this position, the stomal sleeve 318 of the second tool assembly 300 is supported on the anvil head 314 within the vessel portion "VP" distally of the anvil head 314. With the anvil head 314 of the tool assembly 300 positioned within the vessel portion "VP" beneath the layer of skin "S" and the staple cartridge 320 positioned above the layer of skin "S", tissue including a portion of the vessel portion "VP" and the layer of skin "S" and the stomal sleeve 318 are drawn into the tissue gap defined between the staple cartridge 320 and the anvil head 314. As discussed above, the stomal sleeve 318 has a first end portion 321 that is secured to the tissue contact surface 315 of the anvil head 314 at a location radially inwardly of the annular array of staple deforming pockets 319 and a second end portion 54 that is secured to a distal face 324 of the anvil head 314.

Figure 22:
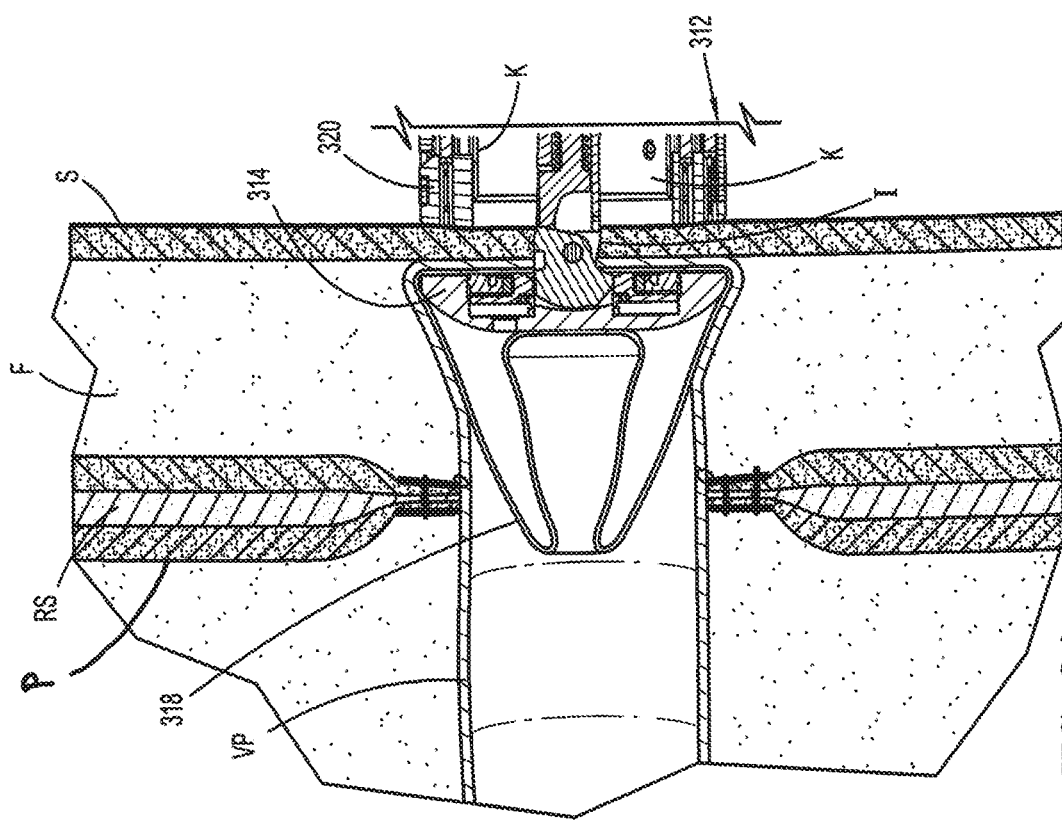
FIG. 22 is a side cross-sectional view of the circular stapling device shown in FIG. 21 with the second tool assembly in the approximated position within the stoma as the second tool assembly is being fired to secure a stomal sleeve beneath a skin layer of the abdominal tissue.

Referring to FIG. 22, after tissue has been drawn into the tissue gap, the stapling device 10 is approximated to clamp tissue between the staple cartridge 320 and the anvil head 314. More specifically, after the tool assembly 300 is properly positioned within the vessel portion "VP" and the incision "I", the anvil head 314 is drawn towards the staple cartridge 320 by rotating the clamping knob 16 in the direction indicated by arrow "B" (FIG. 17). As the clamping knob 16 is rotated, the drive screw 42 is drawn into the hollow sleeve 40 to draw the anvil retainer assembly 32 FIG. 17) into the shell assembly 312 and draw the anvil head 314 towards the staple cartridge 320 to clamp the vessel portion "VP", the layer of skin "S", and other tissue between the anvil head 314 and the staple cartridge 320. As shown, the first end portion 321 of the stomal sleeve 318 which is secured to the tissue contact surface 315 of the anvil head 314 is also clamped between the tissue contact surface 321a of the staple cartridge 320 and the tissue contact surface 315 of the anvil head 314.

In order to fire the stapling device 10, as discussed above with reference to FIG. 18, the firing lockout assembly 22 must be actuated to remove the stop member 124 from within the notch 90 of the drive member 74. In order to actuate the firing lockout assembly 22, the actuator 120 is pressed inwardly in the direction indicated by arrow "C" against the urging of the biasing member 122 to lift the stop member 124 from within the notch 90. When the stop member 124 is lifted from the notch 90, the firing knob 18 can be rotated in the direction indicated by arrow "D" to advance the drive members 74 in the direction indicated by arrow 'E".

As discussed above with reference to FIG. 18, advancement of the drive members 74 advances the pusher member 76 distally within the housing 14 to move the fingers 94 of the pusher member 76 into the shell assembly 312 (FIG. 22) to eject staples 380 (FIG. 22) from the staple cartridge 320 and advance an annular knife "K" to cut tissue. When the staples 380 are ejected from the staple cartridge 320, the staples 380 pass through the layer of skin "S", the vessel portion "VP", and the stomal sleeve 318 to secure the vessel portion "VP" to the inside surface of the layer of skin "S" to create a stoma 400 and to secure the stomal sleeve 318 to the vessel portion "VP" and to the layer of skin "S". Simultaneously, the knife "K" is advanced towards the anvil head 314 to cut the tissue positioned radially inwardly of the annular knife "K" and the first end portion 321 of the stomal sleeve 318 to separate the first end portion 321 of the stomal sleeve 318 from the anvil head 314.

Figure 23:
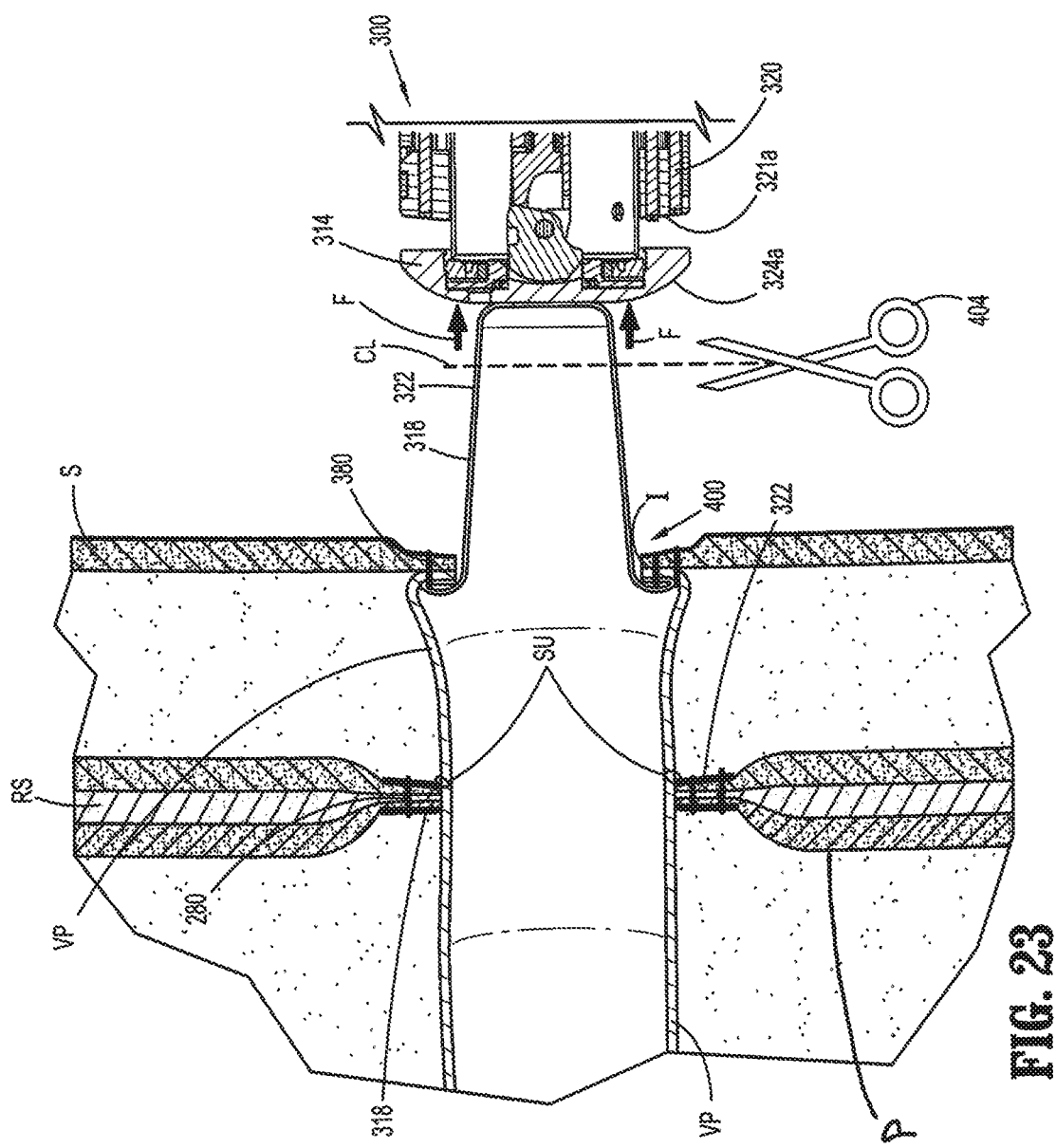
FIG. 23 is a side cross-sectional view of the circular stapling device shown in FIG. 22 after the second tool assembly has been fired and withdrawn from the stoma with the stomal sleeve attached to the second tool assembly and extending through the stoma.

Referring to FIG. 23, after the tool assembly 300 of the stapling device 10 is unapproximated to release the clamped tissue from between the staple cartridge 320 and the anvil head 314, the tool assembly 300 can be withdrawn from the incision "I" in the direction indicated by arrows "F" to withdraw the tool assembly 300 from the stoma 400. As discussed above, the second end portion 322 of the stomal sleeve 318 is attached to the distal face 324a of the anvil head 314. Thus, as the tool assembly 300 is withdrawn from the stoma 400, the second end portion 322 of the stomal sleeve 314 is pulled through the stoma 400 to a position externally of the stoma 400 such that the stomal sleeve 318 defines an internal liner from the within the vessel portion "VP" through the stoma 400.

Figure 24:
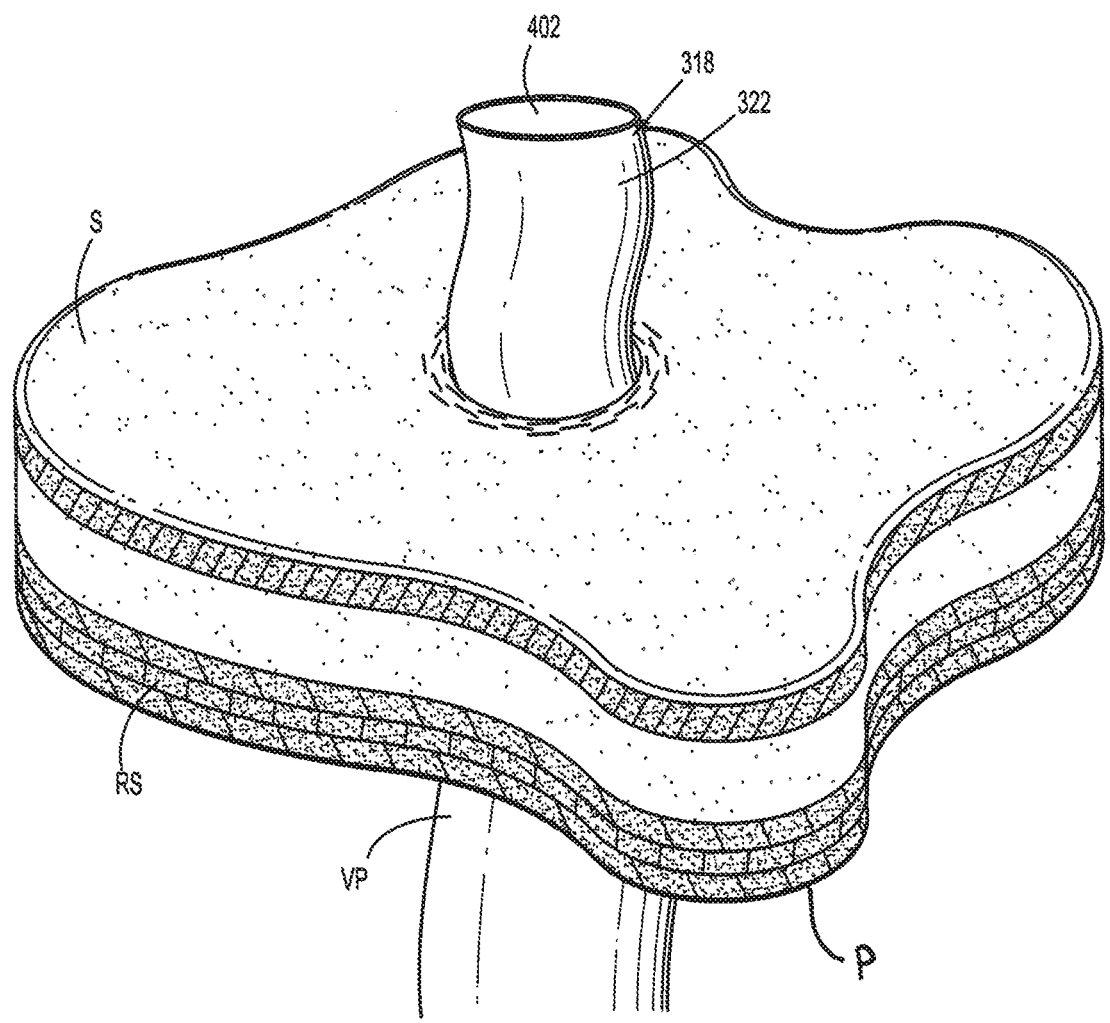
FIG. 24 is a side perspective view of the abdominal tissue with the stomal sleeve separated from the second tool assembly and extending from the stoma.

Referring also to FIG. 24, when the stomal sleeve 318 is positioned externally of the stoma 400, the second end portion 322 of the stomal sleeve 318 can be separated from the anvil head 314 to define an opening or mouth 402 adjacent the second end portion 322 of the stomal sleeve 318. In embodiments, the second end portion 322 of the stomal sleeve 322 is closed and is separated from the anvil head 314 by cutting the second end portion 322 using a scissor or cutting device 404 (FIG. 23) along a cut line "CL". As illustrated, in this position, the stomal sleeve 318 provides an insulative barrier from a position within the vessel portion "VP" through the stoma 400. It is also envisioned that the second end portion 322 of the stomal sleeve 318 may define an opening and be secured to the anvil head 314 by an adhesive. In this embodiment, instead of cutting the second end portion 322 of the stomal sleeve 318, the second end portion 322 of the stomal sleeve 318 can be separated from the distal surface 324 of the anvil head 314 by pulling the second end portion 322 in a direction away from the anvil head 314 to disengage the second end portion 322 from the adhesive on the anvil head 314. Other methods of releasably securing the second end portion 322 of the stomal sleeve 318 to the anvil head 314 are envisioned.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A circular stapling device comprising:
an actuator having a housing including screw threads, a clamping knob, and a firing knob, the firing knob and the clamping knob being rotatably supported on the housing;
an approximation assembly supported within the housing, the approximation assembly including a drive screw and an anvil retainer assembly secured to the drive screw and extending from a distal portion of the housing, the clamping knob being operably associated with the drive screw such that rotation of the clamping knob causes axial movement of the drive screw and the anvil retainer assembly in relation to the housing;
a firing assembly supported within the housing, the firing assembly including at least one drive member and a pusher member engaged with a distal portion of the at least one drive member, the at least one drive member having a proximal portion positioned to be engaged by the firing knob, the firing knob including internal threads engaged with the screw threads on the housing, the firing knob being rotatable about the housing to effect axial movement of the firing knob in relation to the housing, wherein axial movement of the firing knob in relation to the housing causes axial movement of the at least one drive member and the pusher member in relation to the housing; and a tool assembly supported on a distal portion of the housing.

2. The circular stapling device of claim 1, wherein the at least one drive member includes a transverse extension that extends through an opening in the housing, the transverse extension being positioned to engage the firing knob.

3. The circular stapling device of claim 2, wherein the at least one drive member includes first and second drive members.

4. The circular stapling device of claim 2, further including a biasing member positioned to urge the pusher member and the at least one drive member proximally within the housing.

5. A circular stapling device comprising:

an actuator having a housing including screw threads, a clamping knob, and a firing knob, the firing knob and the clamping knob being rotatably supported on the housing, the housing defining an opening;

an approximation assembly supported within the housing, the approximation assembly including a drive screw and an anvil retainer assembly secured to the drive screw and extending from a distal portion of the housing, the clamping knob being operably associated with the drive screw such that rotation of the clamping knob causes axial movement of the drive screw and the anvil retainer assembly in relation to the housing;

a firing assembly supported within the housing, the firing assembly including a drive member and a pusher member engaged with a distal portion of the drive member, the drive member having a proximal portion including a transverse extension that extends through the opening in the housing and is positioned to be engaged by the firing knob, the firing knob including internal threads engaged with the screw threads of the housing, the firing knob rotatable about the housing to effect axial movement of the firing knob in relation to the housing, wherein axial movement of the firing knob in relation to the housing causes axial movement of the drive member and the pusher member in relation to the housing; and a tool assembly supported on a distal portion of the housing.

6. The circular stapling device of claim 5, wherein the drive member includes first and second drive members and the opening includes first and second openings.

7. The circular stapling device of claim 5, further including a biasing member positioned to urge the pusher member and the drive member proximally within the housing.

8. The circular stapling device of claim 7, further including a coupling member positioned between the actuator and the tool assembly.

9. The circular stapling device of claim 8, wherein the biasing member is positioned in compression between the pusher member and the coupling member.

* * * * *